US008119117B2

(12) United States Patent
Deisseroth et al.

(10) Patent No.: US 8,119,117 B2
(45) Date of Patent: Feb. 21, 2012

(54) ADENOVIRAL EXPRESSION VECTOR COMPRISING A CD40L FUSION PROTEIN ADAPTED TO ELICIT CELLULAR IMMUNITY

(75) Inventors: Albert B. Deisseroth, San Diego, CA (US); Lixin Zhang, Muncie, IN (US)

(73) Assignee: VAXum, LLC, Manassas, VA (US)

( * ) Notice: Subject to any disclaimer, the term of this patent is extended or adjusted under 35 U.S.C. 154(b) by 1111 days.

(21) Appl. No.: 10/534,605

(22) PCT Filed: Nov. 12, 2003

(86) PCT No.: PCT/US03/36237
§ 371 (c)(1),
(2), (4) Date: Feb. 12, 2007

(87) PCT Pub. No.: WO2004/044176
PCT Pub. Date: May 27, 2004

(65) Prior Publication Data
US 2007/0269409 A1   Nov. 22, 2007

Related U.S. Application Data

(60) Provisional application No. 60/425,286, filed on Nov. 12, 2002.

(51) Int. Cl.
*A61K 48/00* (2006.01)
*C12N 15/00* (2006.01)
(52) U.S. Cl. .................. 424/93.2; 424/93.6; 424/199.1; 435/320.1
(58) Field of Classification Search .................. None
See application file for complete search history.

(56) References Cited

U.S. PATENT DOCUMENTS

| | | |
|---|---|---|
| 4,161,519 A | 7/1979 | Talwar |
| 4,608,251 A | 8/1986 | Mia |
| 5,658,785 A | 8/1997 | Johnson |
| 5,849,522 A | 12/1998 | Fleckenstein et al. |
| 5,849,876 A | 12/1998 | Linsley et al. |
| 5,874,085 A | 2/1999 | Mond et al. |
| 5,928,913 A | 7/1999 | Efstathiou et al. |
| 5,962,406 A | 10/1999 | Armitage et al. |
| 6,017,527 A | 1/2000 | Maraskovsky et al. |
| 6,040,174 A | 3/2000 | Imler et al. |
| 6,087,329 A | 7/2000 | Armitage et al. |
| 6,110,744 A | 8/2000 | Fang et al. |
| 6,133,029 A | 10/2000 | Gruber et al. |
| 6,147,055 A | 11/2000 | Hobart et al. |
| 6,218,140 B1 | 4/2001 | Fleckenstein et al. |
| 6,224,870 B1 | 5/2001 | Segal |
| 6,284,742 B1 * | 9/2001 | Curiel et al. ............... 514/44 R |
| 6,287,557 B1 | 9/2001 | Boursnell et al. |
| 6,290,972 B1 | 9/2001 | Armitage et al. |
| 6,294,654 B1 | 9/2001 | Bogen et al. |
| 6,440,944 B2 | 8/2002 | Bruder et al. |
| 6,482,407 B2 | 11/2002 | Soo Hoo |
| 6,497,876 B1 | 12/2002 | Maraskovsky et al. |
| 6,500,641 B1 | 12/2002 | Chen et al. |
| 6,566,128 B1 | 5/2003 | Graham et al. |
| 6,794,188 B2 | 9/2004 | Barsov |
| 7,071,172 B2 * | 7/2006 | McCown et al. ............ 514/44 R |
| 7,118,751 B1 * | 10/2006 | Ledbetter et al. .......... 424/192.1 |
| 2002/0068048 A1 * | 6/2002 | Dreyfus et al. ............. 424/93.21 |
| 2003/0176377 A1 | 9/2003 | Xiang et al. |
| 2003/0202963 A1 * | 10/2003 | Crystal et al. ................. 424/93.2 |
| 2004/0147025 A1 * | 7/2004 | Korokhov et al. ............. 435/456 |
| 2005/0048645 A1 * | 3/2005 | Thomas ........................ 435/325 |

FOREIGN PATENT DOCUMENTS

| | | |
|---|---|---|
| WO | WO 96/11279 | 4/1996 |
| WO | WO 98/17799 | 4/1998 |
| WO | WO 2004/044176 | 5/2004 |

OTHER PUBLICATIONS

Hu et al., PNAS 96: 8161-8166, 1999.*
Leonard et al. J. Biol. Chem. 265: 10373-10382, 1990.*
Pruitt et al., Nucleic Acids Research 35: D61-D65, 2007.*
Larsen et al., Bioinformatics 8: 424, 2007.*
Allison and Byars, "Immunological Adjuvants and their mode of action." (in *Vaccines: New Approaches to Immunological Problems*, R. Ellis ed., Chapter 19), pp. 431-449, 1992.
Andrianifahanana, et al., "Mucin (MUC) Gene Expression in Human Pancreatic Adenocarcinoma and Chronic Pancreatitis: A Potential Role of MUC4 as a Tumor Marker of Diagnostic Significance," *Clin Cancer Res.* 7:4033-4040 (2001).
Arai, et al., "Design of the linkers which effectively separate domains of a bifunctional fusion protein," *Protein Engineering*, 14(8):529-532 (2001).
Baruch, et al., "The Breast Cancer-associated MUC1 Gene Generates Both a Receptor and Its Cognate Binding Protein," *Cancer Res.*, 59:1552-1561 (1999).
Biéche, et al., "A gene dosage effect is responsible for high overexpression of the MUC1 gene observed in human breast tumors," *Cancer Genet. Cytogenet.* 98:75-80 (1997).
Bell et al., "Dendritic cells," (in *Advances in Immunology*, edited by Frank J. Dixon, Academic Press, vol. 72), 255-324, 1999.
Broder et al., Recombinant adenovirus-transduced dendritic cell immunization in a murine model of central nervous system tumor Neurosurg Focus 9:1-8, 2000.

(Continued)

*Primary Examiner* — Phillip Gambel
(74) *Attorney, Agent, or Firm* — Jacob Frank; Glenn Snyder

(57) ABSTRACT

Provided are adenoviral vectors for generating an immune response to antigen. The vectors comprise a transcription unit encoding a secretable polypeptide, the polypeptide comprising a secretory signal sequence upstream of a tumor antigen upstream of CD40 ligand, which is missing all or substantially all of the transmembrane domain rendering CD40L secretable. Also provided are methods of generating an immune response against cells expressing a tumor antigen by administering an effective amount of the invention vector. Further provided are methods of generating an immune response against cancer expressing a tumor antigen in an individual by administering an effective amount of the invention vector. Still further provided are methods of generating immunity to infection by human papilloma virus (HPV) by administering an effective amount of the invention vector which enocodes the E6 or E7 protein of HPV. The immunity generated is long term.

50 Claims, 3 Drawing Sheets

OTHER PUBLICATIONS

Byars, et al., "Adjuvant formulation for use in vaccines to elicit both cell-mediated and humoral immunity," *Vaccine* 5:223-228 (1987).
Chen, et al., Linkage of CD40L to a self-tumor antigen enhances the antitumor immune responses of dendritic cell-based treatment. Cancer Immunology Immunother. 51(6) :341-348, 2002.
Choudhury, et al., Dendritic cells derived in vitro from acute myelogenous leukemia cells stimulate antologous, antileukemic T-cell responses. Blood; 93(3) : 780-786, 1999.
Crook et al., Continued expression of HPV-16 E7 protein is required for maintenance of the transformed phenotype of cells co-transformed by HPV-16 plus EJ-*ras*. EMBO J. 8: 513-519, 1989.
Dakappagari et al.; "Chimeric multi-human epidermal growth factor receptor-2 B cell epitope peptide vaccine mediates superior antitumor responses," *J Immuno.* 170(8):4242-4253 (2003).
Dhodapkar, et al. Rapid generation of broad T-cell immunity in humans after a single injection of mature dendritic cells. J Clin Invest.104: 173-180, 1999.
Eck and Turka, Generation of protective immunity against an immunogenic cacinoma requires CD40/CD40L and B7/CD28 interactions but not CD4+ T cells. Cancer Immunology Immunother, 48:336-341, 1999.
Engelmann, et al., Identification and topology of variant sequences within individual repeat domains of the human epithelial tumor mucin MUC1. J. Biol. Chem. 276:27764-27769 , 2001.
Filipe, Mi, "Mucins and gastrointestinal malignancy. A new approach to the interpretation of biopsies," *Acta Med Port* 1:351-365 (1979).
Filipe, Mi, "Mucins in the human gastrointestinal epithelium: a review," *Invest Cell Pathol* 2:195-216 (1979).
Fong L, et al. Dendritic cells injected via different routes induce immunity in cancer patients. J Immunol. 166: 4254-4259, 2001.
Freund, "The mode of action of immunologic adjuvants," *Adv. Tuberc. Res.* 7:130-148 (1956).
Garcon et al., "Universal vaccine carrier. Liposomes that provide T-dependent help to weak antigens," *J. Immunol.* 146:3697 (1991).
Gendler S.J. et al, "Molecular cloning and expression of human tumor-associated polymorphic epithelial mucin," *J. Biol. Chem.* 265:15286-15293 (1990).
Gong, et al., "Selection and characterization of MUC1-specific CD8+ cells from MUC1 transgenic mice immunized with dendritic-carcinoma fusion cells." *Immunology*, 101:316-324 (2000).
Greenlee, et al., "Cancer statistics, 2000," *Cancer J.* 50:7-33 (2000).
Gunzer et al., Dendritic cells and tumor immunity. Semin Immunol 13:291-302, 2001.
Guy, et al. "Expression of the neu protooncogene in the mammary epithelium of transgenic mice induces metastatic disease," *Proc. Natl. Acad. Sci. USA* 89:10578-10582 (1992).
Hollingsworth, et al., "Expression of MUC1, MUC2, MUC3, and MUC4 mucin mRNA in human pancreatic and intestinal tumor cell lines," *Int J Cancer* 57:198-203 (1994).
Hsu et al. Vaccination of patients with B-cell lymphoma using autologous antigen-pulsed dendritic cells. Nat Med. 2: 52-58, 1996.
Jeannon, et al. "Altered MUC1 and MUC2 glycoprotein expression in laryngeal cancer," *Otolaryngol Head Neck Surg.* 124:199-202 (2001).
Johnson, et al., "Characterization of a Nontoxic Monophosphoryl Lipid A," *Rev. Infect. Dis.* 9:S512 (1987).
Kaneda, "New Vector Innovation for Drug Delivery: Development of Fusigenic Non-Viral Particles," *Curr Drug Targets* 4(8):599-602 (2003).
Kim, et al., "Aberrant expression of MUC5AC and MUC6 gastric mucins and sialyl Tn antigen in intraepithelial neoplasms of the pancreas," *Gastroenterology* 123:1052-1060 (2002).
Kontani, et al., "Modulation of MUC1 mucin as an escape mechanism of breast cancer cells from autologous cytotoxic T-lymphocytes," *Br. J. Cancer* 84:1258-1264 (2001).
Kusuhara et al., Killing of naive T cells by CD95L-transfected dendritic cells (DC): in vivo study using killer DC-DC hybrids and CD4(+) T cells from DO11.10 mice. Eur J Immunol 32:1035-1043, 2002.
Lamikanra et al., Regression of established human papillomavirus type 16 (HPV-16) immortalized tumors in vivo by vaccinia viruses expressing different forms of HPV-16 E7 correlates with enhanced CD8(+) T-cell responses that home to the tumor site. J Virol, 75: 9654-9664, 2001.
Larsson et al., A recombinant vaccinia virus based ELISPOT assay detects high frequencies of Pol-specific CD8 T cells in HIV-1-positive individuals. AIDS 13:767-777, 1999.
Liu et al., Codon Modified Human Papillomavirus Type 16 E7 DNA Vaccine Enhances Cytotoxic T-Lymphocyte Induction and Anti-tumor Activity. Virology 15: 301-343, 2002.
Luft et al., IFN-alpha enhances CD40 ligand-mediated activation of immature monocyte-derived dendritic cells. Int Immunol 14:367-380, 2002.
Markowitz and Engleman, Granulocyte-macrophage colony-stimulating factor promotes differentiation and survival of human peripheral blood dendritic cells in vitro. J Clin Invest 85: 955-961, 1990.
Morein, et al., "Iscom, a novel structure for antigenic presentation of membrane proteins from enveloped viruses," *Nature* 308:457 (1984).
Muller, et al., "Single-step induction of mammary adenocarcinoma in transgenic mice bearing the activated c-neu oncodene," *Cell* 54(1):105-115(1988).
Murphy GP, et al. Infusion of dendritic cells pulsed with HLA-A2-specific prostate-specific membrane antigen peptides: a phase II prostate cancer vaccine trial involving patients with hormone-refractory metastatic disease. Prostate 38: 73-78, 1999.
Nestle et al. Vaccination of melanoma patients with peptide- or tumor lysate-pulsed dendritic cells. Nat Med. 4: 328-332, 1998.
Nguyen, et al., "Membrane-bound (MUC1) and secretory (MUC2, MUC3, and MUC4) mucin gene expression in human lung cancer," *Tumor Biol.* 17(3):176-192 (1996).
O'Hagan, et al., "Biodegradable microparticles as controlled release antigen delivery systems," *Immunology* 73:239-242 (1991).
Paglia P, et al. Murine dendritic cells loaded in vitro with soluble protein prime cytotoxic T lymphocytes against tumor antigen in vivo (see comments). J Exp Med 183: 317-322, 1996.
Palucka and Banchereau, Dendritic cells: A link between innate and adaptive immunity. J Clin Immunol. 19:12-25, 1999.
Redmond, et al., "Rotavirus particles function as immunological carriers for the delivery of peptides from infectious agents and endigenous proteins," *Mol. Immunol.* 28:269 (1991).
Regimbald, et al., "The breast mucin MUC1 as a novel adhesion ligand for endothelial intercellular adhesion molecule 1 in breast cancer," *Cancer Res.* 56:4244-4249 (1996).
Ren, et al., "Protein Kinase C Regulates Function of the DF3/MUC1 Carcinoma Antigen in -Catenin Signaling*," *J. Biol. Chem.* 277:17616-17622 (2002).
Retz, et al., "Differential mucin MUC7 gene expression in invasive bladder carcinoma in contrast to uniform MUC1 and MUC2 gene expression in both normal urothelium and bladder carcinoma," *Cancer Res.* 58:5662-5666 (1998).
Ribas et al., C40 cross-linking bypasses the absolute requirement for CD4 T cells during immunization with melanoma antigen gene-modified dendritic cells. Cancer Res. 61:8787-8793, 2001.
Rininsland et al., Granzyme B ELISPOT assay for ex vivo measurements of T cell immunity. J Immunol Methods 240:143-155, 2000.
Rowse, et al., "Tolerance and immunity to MUC1 in a human MUC1 transgenic murine model," *Cancer Res.* 58:315 (1998).
Rudolf et al., Human dendritic cells are activated by chimeric human papillomavirus type-16 virus-like particles and induce epitope-specific human T cell responses in vitro. J Immunol. 166: 5917-5924, 2001.
Shortman K, and Caux C. Dendritic cell development: multiple pathways to nature's adjuvants Stem Cells 15:409-419, 1997.
Skov et al., IL-2 and IL-15 regulate CD154 expression on activated CD4 T cells J Immunol. 164:3500-3505, 2000.
Steinbrink et al., CD4(+) and CD8(+) anergic T cells induced by interleukin-10-treated human dendritic cells display antigen-specific suppressor activity. Blood 99: 2468-2476, 2002.
Tang et al., "Multistep process through which adenoviral vector vaccine overcomes anergy to tumor-associated antigens." Blood, 104:2704-2713, 2004.

Timmerman and Levy, Dendritic cell vaccines for cancer immunotherapy. Annual Rev Med. 50: 507-529, 1999.

Thomas, et al., "Non-viral gene therapy: polycation-mediated DNA delivery," *Appl Microbiol Biotechnol* 62(1):27-34 (2003).

Wang, et al., "Essential roles of tumor-derived helper T cell epitopes for an effective peptide-based tumor vaccine," *Cancer Immun*. 3:16 (2003).

Xiang, et al., "A dual-function DNA vaccine encoding carcinoembryonic antigen and CD40 ligand trimer induces T cell-mediated protective immunity against colon cancer in carcinoembryonic antigen-transgenic mice," *The Journal of Immunology*, 167:4560-4565 (2001).

Yamamoto M., et al., "Interaction of the DF3/MUC1 Breast Carcinoma-associated Antigen and -Catenin in Cell Adhesion," *J. Biol. Chem*. 272:12492-12494 (1997).

Yanagi, et al., "Immuno-gene therapy with adenoviruses expressing fms-like tyrosine kinase 3 ligand and CD40 ligand for mouse hepatoma cells in vivo," *International Journal of Oncology* 22:345-351 (2003).

Yu, et al., "Overexpression of MUC5 genes is associated with early post-operativemetastasis in non-small-cell lung cancer," *Int. J. Cancer* 69:457-465 (1996).

Zhang, et al., "An adenoviral vector cancer vaccine that delivers a tumor-associated antigen/CD40-ligand fusion protein to dendritic cells," *Proc. Natl. Acad. Sci* (USA) 100(25):15101 (2003).

Zheng et al., "Induction of antitumor immunity via intratomoral tetra-costimulator protein transfer," *Cancer Research* 61:8127-8134 (2001).

Zitvogel L, et al. Therapy of murine tumors with tumor peptide-pulsed dendritic cells: dependence on T cells, B7 co-stimulation, and T helper cell 1-associated cytokines. J Exp Med. 183: 87-97, 1996.

Zrihan-Licht S., et al., "Tyrosine phosphorylation of the MUC1 breast cancer membrane proteins. Cytokine receptor-like molecules," FEBS Lett. 356:130-136 (1994).

Zwaveling et al., Established human papillomavirus type 16-expressing tumors are effectively eradicated following vaccination with long peptides. J Immunol, 169:350-358, 2002.

* cited by examiner

ADENOVIRAL EXPRESSION VECTOR COMPRISING A CD40L FUSION PROTEIN ADAPTED TO ELICIT CELLULAR IMMUNITY

CROSS-REFERENCES TO RELATED APPLICATIONS

This application claims the benefit of U.S. Provisional Application Ser. No. 60/425,286 entitled "E7/CD40 Ligand Vector for Induction, Activation, Antigen Loading and Mobilization of Antigen Presenting Cells", filed Nov. 12, 2002, and PCT Application PCT/US2003/036237, entitled "Adenoviral Vector Vaccine", each of which is incorporated by reference herein in its entirety.

FIELD OF THE INVENTION

The present invention relates to the development of immunity against antigen expressing cells using an adenoviral vector that expresses the antigen fused to a secretable form of CD40 ligand.

BACKGROUND OF THE INVENTION

The following discussion of the background of the invention is merely provided to aid the reader in understanding the invention and is not admitted to describe or constitute prior art to the present invention.

The activation of antigen presenting cells (APCs) including the dendritic cells (DCs), followed by loading of the antigen presenting cell with relevant antigens, is a requisite step in the generation of a T cell dependent immune response against cancer cells. Once activated and loaded with tumor antigens, DCs migrate to regional lymph nodes (LNs) to present antigens (ags) to T cells. Very commonly, these APCs express insufficient amounts of surface activation molecules (1) which are required for optimal activation and expansion of T cell clones competent to recognize tumor antigens. Antigen (ag) presentation to naive T cells, in the absence of costimulatory molecule expression on the surface of the APC, leads to anergy of T cells (2). Moreover, cross-presentation by DCs without $CD4^+$ T cell help also results in peripheral deletion of Ag-specific cells in regional LNs (3). In contrast, in the presence of $CD4^+$ T cell help, DCs change their functional ability to cross-prime cells, resulting in clonal expansion of effector T cells (4). This $CD4^+$ T cell help can be replaced with CD40-CD40 ligand (CD40L) interactions (5). CD40L is a 33-kDa type II membrane protein and a member of the TNF gene family which is transiently expressed on $CD4^+$ T cells after TCR engagement (6).

The ability of DCs to generate anti-tumor immune responses in vivo has been documented in a number of animal tumour models (7, 8). However, DC-mediated induction of immunity represents a major therapeutic challenge. The current procedures used for isolating and activating DCs are resource intensive and are difficult to apply to routine clinical practice. In addition, it is difficult to ensure that the antigen presenting cells express appropriate adhesion molecules and chemokine receptors to attract the these DCs to secondary lymphoid organs for priming T cells (9-14).

SUMMARY OF THE INVENTION

In one aspect, the present invention provides an adenoviral expression vector for generating immunity against antigen. The vector comprises a transcription unit encoding a polypeptide comprising, from the amino terminus, a secretory signal sequence upstream of a tumor antigen upstream of CD40 ligand, which is missing all or substantially all of the transmembrane domain, rendering CD40 ligand secretable. The secretory signal sequence functions to direct the tumor antigen-CD40 ligand fusion protein to compartments of the cell which cause the fusion protein to be secreted from the cell.

In one embodiment, the tumor antigen is a human tumor antigen. In another embodiment, the human tumor antigen is the E7 protein of human papilloma virus (HPV).

In some embodiments, the transcription unit includes sequence that encodes a linker between the tumor antigen and the CD40 ligand. Suitable linkers may vary in length and composition.

In another embodiment, the adenoviral expression vector comprises a human cytomegalovirus promoter/enhancer for controlling transcription of the transcription unit.

In still another embodiment, the CD40 ligand is human CD40 ligand.

In yet another embodiment, the CD40 ligand which lacks a functional transmembrane domain is one which contains less than 10% of the transmembrane domain or does not contain a transmembrane domain.

In another aspect, the present invention provides methods of generating an immune response in an individual against cells expressing a tumor antigen by administering an effective amount of the invention vector which encodes the tumor antigen.

In one embodiment, the tumor antigen is a human tumor antigen. In another embodiment, the human tumor antigen is the E7 protein of human papilloma virus.

In yet another embodiment, the cells are cancer cells. In another embodiment, the cancer cells are cervical cancer cells.

In still another embodiment, the method results in the generation of cytotoxic $CD8^+$ T cells against said tumor associated antigen. In another embodiment, the vector following administration is taken up by cells which subsequently secrete a fusion protein encoded by the transcription unit.

In yet another aspect, the present invention provides methods of treating an individual with cancer that expresses a tumor antigen. The method comprises administering to the individual an effective amount of the invention expression vector which encodes the tumor antigen.

In one embodiment, the tumor antigen is a human tumor antigen. In another embodiment, the human tumor antigen is the E7 protein of human papilloma virus.

In yet another embodiment, the cells are cancer cells. In another embodiment, the cancer cells are cervical cancer cells.

In still another embodiment, the method results in the generation of cytotoxic $CD8^+$ T cells against said tumor associated antigen. In another embodiment, the vector following administration is taken up by cells which subsequently secrete a fusion protein encoded by the transcription unit.

In a further aspect, the present invention provides method of generating immunity in a subject to infection by human papilloma virus, comprising administering to the individual an effective amount of the invention adenoviral expression vector wherein the tumor antigen is the E6 or E7 protein of human papilloma virus.

In the above methods, the vector is advantageously administered subcutaneously and may be given on subsequent time to increase the immune response. The immunity against the tumor antigen expressing cells is long lasting.

DETAILED DESCRIPTION OF THE INVENTION

Figure 1:
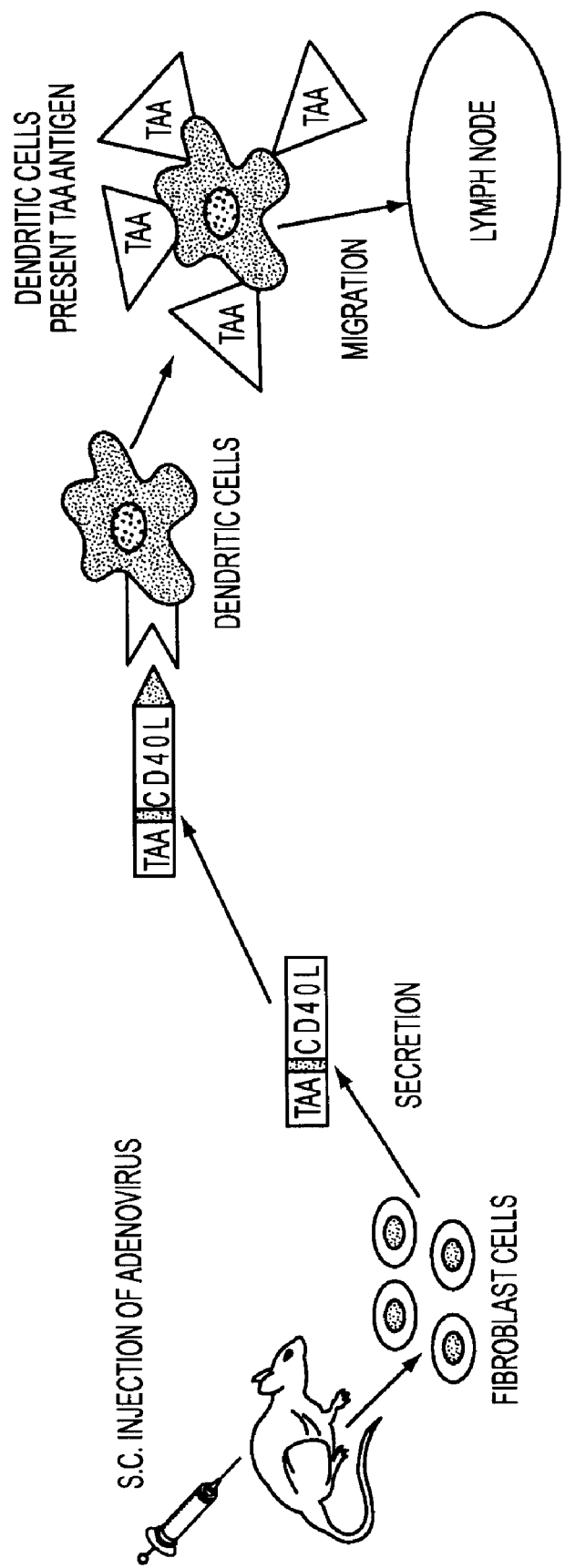
FIG. 1 shows a model for events which follow subcutaneous injection of the secretable tumor antigen/CD40L vector. A proposal for the steps which occur following the injection of the subcutaneous space with respect to the activation, tumor antigen loading, migration to regional lymph nodes, activation of CD8 cytotoxic T cells which are specific for cells carrying the tumor antigen, and induction of a systemic T cell dependent Th1 like immune response.

In order to improve DC activation and tumor antigen loading, an immunization strategy was developed that used a recombinant adenovirus encoding a secretable form of the oncoprotein E7 from high-risk human papilloma viruses (HPV) fused to CD40 ligand from which the transmembrane domain had been deleted. This construct was engineered to be secretable by deleting the cytoplasmic and transmembrane domains from CD40 ligand, which was located downstream from E7 encoding DNA and DNA encoding a signal sequence.

The term "adenoviral expression vector" as used herein, refers to any adenoviral vector that includes exogenous DNA inserted into its genome which encodes a polypeptide. The vector must be capable of replicating and being packaged when any deficient essential genes are provided in trans. An adenoviral vector desirably contains at least a portion of each terminal repeat required to support the replication of the viral DNA, preferably at least about 90% of the full ITR sequence, and the DNA required to encapsidate the genome into a viral capsid. Many suitable adenoviral vectors have been described in the art. U.S. Pat. No. 6,440,944; see U.S. Pat. No. 6,040,174 (replication defective E1 deleted vectors and specialized packaging cell lines. A preferred adenoviral expression vector is one that is replication defective in normal cells.

The term "transcription unit" as it is used herein in connection with the adenoviral expression vector means a stretch of DNA that is transcribed as a single, continuous mRNA strand by RNA polymerase, and includes the signals for initiation and termination of transcription. For example, a transcription unit of the invention is nucleic acid that encodes from 5' to 3' a secretory signal sequence, the E7 protein from HPV and CD40 ligand without its transmembrane domain. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer (see U.S. Pat. Nos. 5,849,522 and 6,218,140).

The term "secretory signal sequence" (aka "signal sequence," "signal peptide," leader sequence," or leader peptide") as used herein refers to a short peptide sequence, generally hydrophobic in charter, comprising about 20 to 30 amino acids which is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the adenoviral expression vector. A variety of suitable such sequences are well known in the art and include the secretory signal sequence of human growth hormone, immunoglobulin kappa chain, and the like.

The term "tumor associated antigen" (TAA) as it is used herein refers to a protein which is present on tumor cells, and on normal cells during fetal life (onco-fetal antigens), after birth in selected organs, or on many normal cells, but at much lower concentration than on tumor cells. A variety of TAA have been described. In contrast, tumor specific antigen (TSA) (aka "tumor-specific transplantation antigen or TSTA) refers to a protein not present on non-tumor cells. TSA usually appear when an infecting virus has caused the cell to become immortal and to express virus antigens. TSAs not induced by viruses can be idiotypes of the immunoglobulin on B cell antigens (TAA) are more common than TSA.

Both TAA and TSA may be the immunological target of an adenoviral expression vector vaccine of the present invention. Unless indicated otherwise, the term "tumor antigen" is used herein to refer collectively to TAA and TSA. A preferred tumor antigen is the E6 or E7 protein of HPV. These antigens are preferably from HPV type 16.

The term "linker" as it used herein with respect to the transcription unit of the adenoviral vector refers to one or more amino acid residues between the carboxy terminal end of the tumor antigen and the amino terminal end of the CD40 ligand (lacking a functional transmembrane domain). The composition and length of the linker may be determined in accordance with methods well known in the art and may be tested for efficacy. The linker is generally from about 3 to about 15 amino acids long, more preferably about 5 to about 10 amino acids long, however, longer or shorter linkers may be used or the linker may be dispensed with entirely.

The term "CD40 ligand" as used herein refers to a type II membrane polypeptide having an extracellular or cytoplasmic domain at its N-terminus, a transmembrane region and an extracellular domain at its C-terminus. CD40L is a member of the tumor necrosis factor superfamily of molecules and carries the designation TNF5. Unless otherwise indicated the full length CD40L is designated herein as "CD40L," "wtCD40L" or "wtTmCD40L." The form of CD40L where the cytoplasmic domain has been deleted is designated herein as "ΔCtCD40L." The form of CD40L where the transmembrane domain has been deleted is designated herein as "ΔTmCD40L." The form of CD40L where both the cytoplasmic and transmembrane domains have been deleted is designated herein as "ΔCtΔTmCD40L." The nucleotide and amino acid sequence of CD40L from mouse and human is well known in the art and can be found, for example, in U.S. Pat. No. 5,962,406 (Armitage et al.).

Murine CD40L (mCD40L) is 260 amino acids in length. The cytoplasmic (Ct) domain of mCD40L extends approximately from position 1-22, the transmembrane domain extends approximately from position 23-46, while the extracellular domain extends approximately from position 47-260.

Human CD40L (hCD40L) is 261 amino acids in length. The cytoplasmic domain of hCD40L extends approximately from position 1-22, the transmembrane domain extends approximately from position 23-46, while the extracellular domain extends approximately from position 47-261.

The phrase "CD40 ligand is missing all or substantially all of the transmembrane domain rendering CD40 ligand secretable" as it is used herein refers to a recombinant form of CD40 ligand that can be secreted from a cell. The transmembrane domain of CD40L containing about 24 amino acids in length functions to anchor CD40 ligand in the cell membrane. CD40L from which all of the transmembrane domain has been deleted is CD40 ligand lacking residues 23-46. CD40 ligand missing substantially all of the transmembrane is one that contains 6 residues or less of sequence at one end of the transmembrane domain, more preferably less than about 4 residues of sequence at one end of the transmembrane domain, even more preferably less than about 2 residues of sequence on one end of the transmembrane domain, and most preferably 1 residue or less on one end of the transmembrane domain. Thus, a CD40L that lacks substantially all of the transmembrane domain rendering the CD40L secretable is one that contains no more than six residues of sequence on one end of the domain. Such as CD40L would contain, in addition to the extracellular domain and optionally the cytoplasmic domain, no more than amino acids 41-46 or 23-28 located in the transmembrane domain of CD40L.

It should be understood that a CD40L which lacks a functional transmembrane domain may still include all or a portion of the cytoplasmic domain. Likewise, a CD40L which lacks a functional transmembrane domain may include all or a substantial portion of the extracellular domain.

As used herein, an adenoviral vector of the present invention can be administered as a vaccine to induce immunity to a tumor associated antigen. The viral vector may be formulated as appropriate with a pharmaceutically acceptable carrier. Accordingly, the viral vectors may be used in the manufacture of a medicament or pharmaceutical composition. Viral vectors of the invention may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol sodium chloride, sodium citrate, and the like.

Alternately, viral vectors may be prepared for oral administration. Pharmaceutically acceptable solid or liquid carriers may be added to enhance or stabilize the composition, or to facilitate preparation of the viral vectors. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. When a liquid carrier is used, the preparation may be in the form of a syrup, elixir, emulsion, or an aqueous or non-aqueous suspension.

Viral vectors of the invention may be formulated to include other medically useful drugs or biological agents. The viral vectors also may be administered in conjunction with the administration of other drugs or biological agents useful for the disease or condition that the invention compounds are directed.

As employed herein, the phrase "an effective amount," refers to a dose sufficient to provide concentrations high enough to generate an immune response in the recipient thereof. The specific effective dose level for any particular subject will depend upon a variety of factors including the disorder being treated, the severity of the disorder, the activity of the specific compound, the route of administration, the rate of clearance of the viral vectors, the duration of treatment, the drugs used in combination or coincident with the viral vectors, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed, Pergamon Press, 1990; and Remington's Pharmaceutical Sciences, 17th ed., Mack Publishing Co., Easton, Pa., 1990. For administration of adenoviral vectors, the range of particles per administration typically if from about $1 \times 10^7$ to $1 \times 10^{11}$, more preferably $1 \times 10^8$ to $5 \times 10^{10}$, and even more preferably $5 \times 10^8$ to $2 \times 10^{10}$. A viral vector can be administered parenterally, such as intravascularly, intravenously, intraarterially, intramuscularly, subcutaneously, or the like. Administration can also be orally, nasally, rectally, transdermally or inhalationally via an aerosol. The viral vectors may be administered as a bolus, or slowly infused. The vector is preferably administered subcutaneously.

The E7 protein derived from the human papillomaviruses (HPVs) was chosen as the exemplary TAA since it has been shown to be a strong stimulus of the cellular immune response, and to be expressed on every cell of a tumor population which is generated from HPV transformed tissue. HPV can cause a variety of epithelial lesions of the skin and genital tract. HPV related diseases of the genital tract constitute the second leading cause of cancer death among women in the world. These include genital warts, cervical intraepithelial neoplasia (CIN) and cancer of the cervix. The HPV type most commonly associated with high grade CIN and cervical cancer is HPV type 16. The majority of cervical cancers express the non-structural HPV16-derived gene products E6 and E7 oncoproteins. In HPV-induced cervical cancer model, the E6/E7 oncoproteins are required for maintenance of the malignant phenotype and their expression correlates with the transforming potential of HPV16 (15-16). Therefore, E6 and E7 represent a target of choice for the therapeutic vaccination (17-19).

The results herein show that the subcutaneous injection of this vector leads to; 1) Local infection of cells surrounding the needle tract; 2) Secretion of the chimeric E7/CD40L transmembrane less fusion protein over a 10 day period from the vector injected cells; 3) Binding of the fusion protein to APCs leading to activation of the APC's and E7 presentation; 4) Migration of the loaded and activated APCs to regional lymph nodes, and 5) Evolution of T cell dependent systemic immunity to cell lines carrying the tumor associated antigen which extends for greater than one year.

Generation of cytotoxic T cell lymphocytes specific for individual populations of tumor cells by antigen presenting cells (dendritic cells) depends on the activation of expression of co-stimulatory molecules. One of the mechanisms through which this can occur is the binding of the CD40 ligand on the plasma membrane of CD4 Helper T Cell lymphocytes to the CD40 receptor on the dendritic cells. Following this activation, dendritic cells migrate to region lymph nodes or to the spleen in which the presentation of the peptides derived from tumor associated antigens induces the activation and expansion of CD8 cytotoxic T cell lymphocyte clones which are competent to recognize the tumor associated antigen.

The evolution of such CD8 cytotoxic T cell lymphocytes, which can recognize tumor associated antigens on tumor cells, which leads to the killing of the tumor cells bearing these antigens, is limited by many factors. One factor is the low level of transfer of the tumor associated antigens from tumor cells into the antigen presenting cells. Another is the failure to induce the co-stimulatory molecules on the antigen presenting cells which are necessary for sustained activation and expansion of tumor antigen specific CD8 cytotoxic T cell lymphocytes which are competent to recognize and kill the tumor cells.

Antibodies which bind to the CD40 receptor on antigen presenting cells can activate the expression of the co-stimulatory molecules in the antigen presenting cells. In vitro infection of the antigen presenting cells (either dendritic cells or tumor cells themselves) with an adenoviral vector (Ad-wtTmCD40L) which carries a CD40 ligand transcription unit has also been used to activate co-stimulatory molecule expression on the antigen presenting cells or the tumor cells (crystal). Injection of these dendritic cells into the tumor nodules or injection of the irradiated Ad-wtTmCD40L infected tumor cells into immunocompetent mouse hosts carrying tumor nodules can lead to regression of the tumor nodules and to increased survival.

In addition, in vivo generation of tumor antigen specific CD8 cytotoxic T cell lymphocytes results from in vitro "loading" of the antigen presenting cells with tumor associated antigens by incubation with tumor antigen peptide fragments, or with the tumor cells themselves, or with adenoviral vectors which carry transcription units encoding the tumor associated antigens, followed by injection of the antigen loaded antigen presenting cells.

In order to develop a more efficient way of generating a tumor antigen CD8 cytotoxic T cell lymphocyte dependent systemic immune response to tumor associated antigens, it was hypothesized that the continuous release of a protein in the subcutaneous space of immunocompetent animals, which was capable of both activating the expression of co-stimulatory molecules in antigen presenting cells and at the same time delivering tumor associated antigen into the intracellular space of antigen presenting cells over a 10 day period, could lead to a very strong CD8 cytotoxic T cell lymphocyte response against the tumor cells bearing the tumor associated antigen.

The fusion protein transcription unit that was chosen to test this hypothesis comprised a tumor associated antigen (the human papilloma virus E7 transforming protein) linked to the amino-terminal end of the CD40 ligand. This protein was engineered to be secreted from cells in which it was being made by deleting the transmembrane and cytoplasmic domains of the CD40 ligand, and attaching a human growth hormone signaling domain to the amino-terminal end of the E7 tumor antigen portion of the fusion protein gene. Subcutaneous injection of an adenoviral vector which carried a transcription unit encoding this secretory form of the tumor associated antigen/CD40 ligand fusion protein (Ad E7-ΔCtΔTmCD40L) was chosen to generate adenoviral infected cells in the subcutaneous space of a subject.

It was reasoned that the cells infected in the vicinity of the site of subcutaneous injection of the vector, would release the tumor antigen/CD40 ligand secretory protein for up to 10-14 days (the time period during which most adenoviral vector infected cells produce the protein product of the transgene). Antigen presenting cells (e.g. DC) in the vicinity of the infected cells at the injection site would take up E7 tumor associated antigen, which would be digested in the proteosome with the resultant E7 peptides trafficking to the endoplasmic reticulum where they would bind to Class I MHC molecules. Eventually, the DCs would present the E7 tumor associated antigen on the surface in the Class I MHC molecule. Activated, tumor antigen-loaded antigen presenting cells would migrate to lymphocyte bearing secondary organs such as the regional lymph nodes or the spleen. During the two weeks of continuous release of the tumor antigen/CD40 ligand fusion secretory protein, CD8 cytotoxic T cell lymphocytes which were competent to recognize and kill cells, which carried the tumor associated antigens, would be expanded in the lymph nodes and spleen by the presence of the activated and antigen loaded dendritic cells. The continuous nature of the stimulation and the expansion of the tumor antigen specific cytotoxic T cells by the continuous release from the vector infected cells was believed to generate an immune response which would be greater in magnitude than were possible using a vector which carried a tumor associated antigen/CD40 ligand which was non-secretory. An outline of the events that would occur during the release of secretable form of the E7/CD40L are shown in FIG. 1. The constant release of the fusion protein and the resultant continuous entry of activated DCs bearing the E7 peptides into the regional lymph nodes was believed to provide an more effective in vivo way to generate a strong and durable T cell dependent systemic immune response against E7 positive tumor cells than injection of a vector which expresses E7 alone or CD40L alone, or a vector that expresses E7/CD40 ligand transcription where CD40L is not secretable.

The results of the experiments described herein were designed to test these hypotheses and confirmed all the predictions. Subcutaneous injection of a replication incompetent adenoviral vector, which carries a secretory form of the E7 tumor associated antigen/CD40 ligand protein, induced a very robust and long lasting CD8 cytotoxic T cell lymphocyte dependent systemic immune response against cancer cells which carry the E7 tumor associated antigen. Indeed, the experimental results showed that the vector expresses the secretory form of the tumor associated antigen/CD40 ligand fusion protein generated an immune response which is much stronger than the subcutaneous injection of a vector that expresses the non-secretory form of the E7 tumor associated antigen/CD40 ligand fusion protein. It is clear from the these experimental results that the subcutaneous injection of vectors encoding the tumor associated antigen/CD40 ligand secretory fusion protein produces an immune response that is much stronger than occurs following the subcutaneous injection of the vector which carries transcription units encoding only for the E7 tumor associated antigen or the CD40 ligand (secretory or non-secretory).

In addition, it was shown that the local release of the fusion protein generates activation of antigen presenting cells, and their migration to the lymphoid bearing secondary organs. Finally, it was demonstrated herein that the immunological resistance generated by the subcutaneous injection of adenoviral vectors carrying the E7 tumor associated antigen/CD40 ligand secretory transcription unit was specific to cells carrying the tumor associated antigen and was long lasting for up to one year after the vector injection. Although not wishing to be bound by any theory, it is believed that the invention method of linking the tumor associated antigen to a secreted form of CD40 ligand creates a protein which can at the same time both activate antigen presenting cells and antigen load them in vivo avoiding the expense and the logistical problems associated with in vitro generation of antigen presenting cells or cytotoxic T cell lymphocytes.

A second advantage is that the use of the secreted tumor associated antigen/CD40 ligand fusion protein for activation and antigen loading may result in selective binding to the antigen presenting cells and transport of the antigen into the intracellular space of the antigen presenting cell. This would solve the problem of delivering sufficient tumor antigens into the intracellular space of a subject which is frequented by antigen presenting cells so as a sufficient density of tumor associated peptide on the plasma membrane of the antigen presenting cells for generating a strong cytotoxic-T cell lymphocyte response against the tumor associated antigen expressing tumor cell.

A third advantage is that the presence of the CD40 ligand in the secreted protein may activate co-stimulatory antigen expression on the antigen presenting cell, thus making the activation independent of initial CD4 T cell lymphocyte help.

A fourth advantage of the secretory nature of the viral fusion protein transcription unit is that there may be continuous release of the activating and antigen loading fusion protein in the space populated by antigen presenting cells over a 10 day period. This may account in part for the robustness of the immune response observed and its durability.

The decision to utilize the HPV E7 protein as the tumor associated antigen of the fusion protein was motivated by several factors. The first is that the E7 protein has been shown to be transforming and essential for the continued proliferation of HPV transformed cells. This property of E7 ensures that most if not all of the cells in the population would carry the antigen. In addition, the choice of a DNA virus transforming protein as the tumor associated antigen was designed to make the experiments unambiguous with respect to the testing of the value of the secretory fusion transcription unit. A separate but important reason for selecting HPV E7 as the tumor associated antigen in the invention vector was to evaluate the ability of E7 to prevent the infection and proliferation of HPV infected cervical epithelial. If such vector could generate an immune response against HPV infected cells, then individuals in whom such a reaction would be generated would be immune and resistant to the infection of the human papilloma virus.

Human papillomavirus (HPV) infection induces a natural host immune response that is not sufficient to eliminate infection. One reason for this is that there are over 100 genotypes of HPV each of which may have a unique amino acid sequence and therefore unique epitopes that allow the virus to escape detection by individuals exposed to other HPV genotypes. A second reason is that there are a small number of individuals who are unable to mount a cellular immune response to HPV infected cells. Such individuals may be the ones in whom chronic HPV infections develop which lead to cervical dysplasia and to invasive cervical cancer. In addition, 60% of human cervical cancers are related to infections with the HPV 16 genotype. Up to 95% of cervical cancer cases are attributable to HPV infections. The second leading cause of cancer death among women worldwide is HPV associated malignancies. In emerging nations of the world, HPV associated malignancies represent the leading cause of death among women between the ages of 25 and 35.

In order to amplify an immune response to the HPV infected cells so as to develop immunity to HPV infection, several methods have been attempted. The therapeutic peptide and protein-based vaccines (15), DNA (16) and viral vector-based vaccines (17), modified tumor cell (18) and dendritic cell-based vaccines (19) all have been previously investigated and reported to generate immune responses to human HPV-associated neoplasms in animal models. These previous studies have shown that a variety of preparation of DCs can stimulate an effective antitumor immunity, including DCs loaded with proteins, DCs fused with tumor cells and DCs transduced with tumor-derived RNA or viral vectors (20, 21, 22). At present, in vitro CD40 ligand activation of MART-1 gene modified DC can promote CD8 T cell lymphocyte mediated immunity to melanoma cells (23). Injection of CD40 ligand-transduced tumor showed a therapeutic effect against the established MCA205 brain tumor cell line (24). These studies indicated that DCs that were loaded with antigen and activated at the same time can provide strong protective immunity.

Recombinant adenoviral vectors offer a potentially superior approach that allows a higher efficiency of gene transfer than that of DNA vaccines. Adenoviral vectors encoding tumor associated antigens also can induce the protective cellular and humoral immunity against such antigens, including those to which tolerance had developed.

Replication-defective adenoviral vectors, used herein to generate continual local release of a fusion protein composed of a tumor antigen (E7) linked to a secretory form of CD40 ligand, facilitated DCs maturation, promoting the development of effective antigen-specific immunity. It was demonstrated that secretable E7-ΔCtΔTmCD40L construction dramatically enhances the potency of the cellular immune response to E7 positive tumor cells. Subcutaneous injection of the Ad E7-ΔCtΔTmCD40L vector elicited strong E7-specific $CD8^+$ T cell-mediated immunity, which could prevent the engraftment of cancer cells which express the E7 tumor associated antigen.

Although not wishing to be bound by any theory, a potential mechanism for the observed enhancement of E7-specific $CD8^+$ T-cell activity following injection of the vector encoding the tumor antigen/secretable CD40L is the enhanced activation and migration of dermal professional APCs which are generated by the subcutaneous release of fusion protein from vector infected cells. In contrast to the strategy of loading DCs with antigen by administering the antigen, secretion of the E7-ΔCtΔTmCD40L protein, by the dermal fibroblasts or other cells in the subcutaneous space may more effectively activate and load local APCs, which may be effective in activating systemic T-cell immunity.

Another factor potentially affecting enhancement of antigen-specific CD8+ T cell activity by the AdE7-ΔCtΔTmCD40L vector is the use of the full-length E7 protein as the tumor associated antigen. Some workers have compared immune responses achieved with vaccines based on either HPV cytolytic T lymphocyte (CTL) plus helper T lymphocyte epitopes or the CTL epitope alone derived from the E7 peptide of the HPV16 strain The results showed that the E7-specific CD8+ response was significantly greater for the vaccine based on HPV epitopes plus helper Th epitopes than for the vaccine based only on the CTL epitope (15).

In summary, the findings illustrate that linkage of ΔTmCD40L, which is a secretory form of a CD40L, to a tumor associated antigen, can lead to enhanced antigen-specific CD8+ T-cell activity in vivo.

The following examples serve to illustrate the present invention. These examples are in no way intended to limit the scope of the invention.

EXAMPLES

1. Construction of Adenoviral Expression Vectors

The transcription unit, E7-ΔCtΔTmCD40L, of the adenoviral vector encoded a signal secretory sequence followed by the HPV type 16 E7 gene which was connected via a linker to the fragment of the CD40 ligand which contained the extracellular domain without the transmembrane or cytoplasmic domains. E7 was small enough that it did not disrupt the natural assembly of a homotrimeric array trimeric of the native wild type CD40 ligand. The fusion protein was engineered to be secreted from vector infected cells by the addition of a signal sequence to the amino-terminal end of the E7 protein and by deletion of the transmembrane and cytoplasmic domains of the CD40 ligand.

The transcription unit was introduced into the E1 gene region of the adenoviral vector backbone. After the adenoviral vector particles were generated in HEK 293 cells, the vector DNA was purified by cesium chloride gradient centrifugation. The presence of the signal peptide in the adenoviral vector was confirmed by restriction enzyme analysis and by DNA sequencing.

Adenoviral vectors with different transcription units including Ad-E7-ΔTmCD40L, Ad-E7-wtTmCD40L Ad-ΔTmCD40L, Ad-wtTmCD40L, and Ad-GFP-ΔTmCD40L were constructed (see materials and methods) (GFP refers to green fluorescent protein).

2. Cell Free Expression Adenoviral Vector Transcription Units

An in vitro cell free transcription/translation system was used to confirm that the adenoviral vector containing transcription unit encodes the correct molecular weight protein. The results summarized in Table I show that the proteins produced by the in vitro transcription/translation reactions using PCR-generated cDNAs as templates migrated as expected with the following molecular weights: the E7-ΔCtΔTmCD40L is 32 kDa, E7-wtCD40L is 39 kDa, and the ΔCtΔTmCD40L is 22 kDa.

3. Western Blot Analysis of the Proteins in Cells 293 Infected by the Recombinant Adenovirus Western blot analysis was used to evaluate the proteins expressed in cells infected with the different adenoviral vectors. The results summarized in Table I show that molecular weights of the proteins produced in the vector infected cells from the Ad-E7-ΔCtΔTmCD40L vector, the Ad-wtTmCD40L vector, the Ad-GFP-ΔCtΔTmCD40L vector, the Ad-wtTmCD40L, and the Ad-ΔCtΔTmCD40L vectors are respectively. 32 kDa, 35 kDa, 50 kDa, 39 kDa and 22 kDa These data confirm that the transcription units are structurally correct and that the vector DNA in each case can be transcribed and translated into protein at sufficient levels to be detected in a Western blot.

TABLE I

Molecular weight of viral vector translation products

| Vector | Molecular Weight Cell Free Transcription Translation | Molecular Weight by Western |
|---|---|---|
| Ad-E7-ΔCtΔTmCD40L | 32 kDa | 32 kDa |
| Ad-E7-CD40L | 39 kDa | 32 kDa |
| Ad-ΔCtΔTmCD40L | 22 kDa | 22 kDa |
| Ad-CD40L | 37 kDa | 37 kDa |
| Ad-GFP-ΔCtΔTmCD40L | Not Done | 50 kDa |

4. Comparison of the Adenoviral Expression Vectors for Efficiency of Activation of DCs The various adenoviral vectors were compared for efficiency of activation of DC cells. For this purpose, bone marrow derived DCs were exposed in vitro to each of the vectors, under conditions that result in infection of close to 100% of the test cells (293 cells). After 48 hours, the cells were reacted with antibodies to activation markers CD80 and CD54 and evaluated in a fluorescent activated cell sorter. The percentage of cells positive for the CD80 and CD54 activation markers on the DCs exposed to the vectors carrying the secretable CD40L transcription units (either the E7/CD40L or the CD40L) was far above that seen with the DCs exposed to the vectors carrying either of the non-secretable CD40L transcription units (wtTmCD40L, or E7/wtTMCD40L), or the Ad-GFP vector as shown below in Table II.

TABLE II

Expression of Activation Markers on DC

| | Percent CD 80+ | Percent CD54+ |
|---|---|---|
| AdE7-wtCD40L | 15.27% | 17.66% |
| AdE7-Δ TmCD40L | 40.4% | 38.6% |
| Ad GFP | 4.63% | 3.87% |

These results indicate that the adenoviral vector with the secretable CD40L transcription unit is much more efficient in activating DCs in vitro than the vectors carrying the non-secretable transcription units.

5. Comparison of IL-12 and IFN-γ Cytokine Release from DCs Infected by Adenoviral Expression Vectors Activation of DCs as measured by the release of cytokines IL-12 and IFN-gamma was determined for the various adenoviral vector transcription units. A statistically significant difference in the level of induction of IL-12 production following exposure of the DCs to the Ad-E7-ΔCtΔTmCD40L and Ad-E7-CD40L vectors was observed (P<0.0001). Specifically, 18±4 pg/2×$10^5$ cell/ml/24 h and 88±29 pg/2×$10^5$ cell/ml/48 h of IL-12 were produced by the DCs exposed to the AdE7-ΔCtΔTmCD40L vector, whereas exposure of DCs to the Ad-E7-CD40L vector, produced 0 pg/2×$10^5$ cell/ml/24 h and 7 pg/2×$10^5$ cell/ml/48 h of IL-12.

Similarly, there was a statistically significant difference in the amount of IFN-γ released by DCs exposed to the Ad-E7-ΔCtΔTmCD40L vector (335±29 pg) as compared to DCs exposed to the Ad-CD40L vector (186±9 pg) in first 24 hours (P<0.0001). However, there was no significant difference between the level of IL-12 produced by DCs exposed to the vectors containing the secretable vs the non-secretable E7/CD40L transcription units at 48 hours.

These data indicate that the Ad-E7-ΔCtΔTmCD40L vector is more efficient at inducing a cytokine release from the DCs than the Ad-E7-CD40L vector or the other control vectors. In addition, since the secreted tumor antigen/CD40 ligand complex should engage the CD40 receptor on dendritic cells to effect cytokine release, these results suggest that the E7-ΔCtΔTmCD40L fusion protein forms a functional trimeric molecule at its carboxyl-terminal end to engage the CD40 receptor.

6. Determination of Cancer Immunity Developed by Adenoviral Expression Vectors

To assess the efficacy of the Ad-E7-ΔCtΔTmCD40L vector for prevention of engraftment of the E7 positive TC-1 cell line in C57BL/6 mice, 1×$10^8$ pfu of each vector was injected subcutaneously into mice. Seven days later, a repeat (boost) dose of the same vector was given. One week after the last vaccination, 5×$10^5$ TC-1 cells were injected subcutaneously on the back of the C57BL/6 mice at a site separate from the which vector injection site. Following Ad-E7-ΔCtΔTmCD40L vector injection, all of the mice were tumor free at day 108 after tumor challenge. In contrast, following injection with Ad-ΔCtΔTmCD40L; Ad-CD40L; Ad-E7-CD40L, all (5/5) mice developed tumors within 15 days after tumor challenge, and all had died by day 42.

To characterize the types of effector cells involved in the suppression of tumor growth, mice were depleted of CD4 or CD8 T cells by antibody treatment prior to vaccination with Ad-E7-ΔCtΔTmCD40L. Antibody treatment continued even after the TC-1 challenge to ensure proper depletion of the T cells subsets. It was observed that a TC-1 tumor grew in the mice that were depleted of either the CD4 or CD8 T cells. This suggests that presence of both CD4 and CD8 T cells are important for the antitumor effect induced by Ad-E7-ΔCtΔTmCD40L.

7. DC Binding of Fusions Proteins Expressed by Adenoviral Expression Vectors.

To test whether the secretable E7-ΔCtΔTmCD40L protein binds to DCs in the areas close to the site of vector injection, as predicted in the model in FIG. 1, the skin at the site of intradermal injection of the Ad-E7-ΔCtΔTmCD40L vector was sectioned and double stained these sections with antibodies to the CD40L, and the DC markers CD80 and MHC-II. A widespread distribution of double-staining was observed in the epidermis from mice vaccinated with Ad-E7-ΔCtΔTmCD40L and Ad-ΔCtΔTmCD40L vectors. These results showed soluble E7-ΔCtΔTmCD40L protein binding to the surface of DCs following injection of the Ad-E7-ΔCtΔTmCD40L. In contrast, only a few positive cells were observed in the epidermis following injection of the Ad-E7-CD40L, and the Ad-E7-CD40L vectors in the vaccinated mice at 3 days after the vector injection. These results indicate that the injection of the vector carrying the secretable form of the E7/CD40L is much more effective in generating protein that binds to the DCs than is the E7/CD40L protein that does not contain the signal peptide and has the transmembrane domain. The use of the vector carrying the E7/ΔTmCD40L transcription unit which encodes a secreted form of the protein appears to amplify the effect of the vector from the infected DCs to a much larger population of DCs. The results suggest that the injection of the vector carrying the secretable form of the E7/CD40L protein will generate much higher levels of activated DCs loaded with the E7 than injections of vector carrying the non-secretable form of this protein. This prediction was tested directly in the next section.

8. Evaluation of DCs Migration In Vitro and In Vivo Induced by Vaccination Using Adenoviral Expression Vectors Following the binding of the CD40 ligand to the CD40 receptor, internalization of the tumor antigen/CD40 ligand-CD40 receptor complex and the subsequent digestion and processing of tumor antigen peptides, the DCs migrate to secondary lymphoid organs-regional lymph nodes to become mature DCs. In that location, the activated/antigen loaded DCs can present the tumor associated antigenic peptides and stimulate naïve CD4 helper T cells and amplify CD8 cytotoxic T cell lymphocytes (CTL) which are selectively toxic for cancer cells which carry the tumor associated antigen.

In order to test if the injection of AdE7-ΔCtΔTmCD40L vectors induced such a migration of the DCs to the regional lymph nodes in vivo, DCs that were derived in vitro from bone marrow cells were labeled by the supravital dye CFSA and then exposed to vector Ad-E7-CtΔTmCD40L, Ad-E7-CD40L, Ad-ΔCtΔTmCD40L and Ad-CD40L under conditions (100 MOI) designed to generate 100% infectivity. The infected dye loaded DCs were injected into the left flank of the C57BL/6 mice. Three days after these injections, the mice were sacrificed and the axillary lymph nodes on either side were harvested and studied for the presence of the dye loaded DCs. CFDA SE stained DC's carrying the secretable E7/CD40L transcription unit were observed in the regional lymph nodes, whereas CFDA SE stained DC's carrying the E7/CD40L transcription unit were not observed in regional lymph nodes.

9. Evaluation of the Immune Response Elicited Following Administration of Adenoviral Expression Vectors CD8+ T cell lymphocytes are involved in protective immune responses to infected or tumor cells. It was examined whether E7-specific CD8+ T cells were induced by subcutaneous injection of C57BL/6 mice with the Ad-E7-ΔCtΔTmCD40L vector. CD8+ T cell responses were assessed using cytotoxicity assays and the detection of antigen-specific CTLs using the enzyme-linked immunospot (ELISPOT) assay.

Mice were given two subcutaneous injections with the following vectors: (1) Ad-E7-ΔCtΔTmCD40L; (2) Ad-CD40L; (3) Ad-E7-CD40L; (4) Ad-ΔCtΔTmCD40L; and (5) negative control. Spleen cells from vector injected mice were stimulated by exposure to the TC-1 cells at a ratio of 25 TC-1 cells to one spleen cell for 48 hours. The restimulated spleen cells were then plated in 96 cell nitrocellulose filter plates which had been coated with antibodies to either interferon gamma or IL-4. Following the washing of the wells with saline, the ELISPOT assay was carried out. The results of the ELISPOT indicated that the subcutaneous injection of the vector carrying the secretable E7/CD40L protein significantly increased MHC class I-restricted CTLs that were detectable with IFN-γ in spleens to a degree which was greater than that seen following injection of the vector carrying the non-secretable E7/CD40L transcription unit or other control vectors. Also, the frequency of cells producing the T1-type cytokine IFN-γ (117±10.61) was significantly higher than frequency of splenocytes capable of secreting a Th2 cytokine such as IL-4 (22.3±3.68). These data indicate that the E7-ΔCtΔTmCD40L vector vaccination stimulates a Th1 rather than a Th2 immune response.

To determine if CD8 T cell lymphocyte effector cells specifically toxic for cancer cells bearing the E7 antigen were generated following injection of C57BL/6 mice following injection of the vector carrying the secretable E7/CD40L vector, splenocytes obtained animals given two subcutaneous injections of vector were incubated in vitro with mitomycin C-treated TC-1 cells for 5 days for restimulation. Restimulated effector cells were mixed with TC-1 or control target cells for 4 hours and the release of LDH was measured. It was observed that spleen cells from mice injected with the Ad-E7-ΔTm CD40L vector lysed 90% of the TC-1 target cells. No apparent lysis was observed against irrelevant but syngeneic EL-4 cells, which do not carry the E7 antigen. The level of cytotoxicity to TC-1 cells was higher with splenocytes taken from the Ad-E7-ΔCtΔTmCD40L vector inject mice than with splenocytes taken from mice previously injected with the Ad-E7-CD40L vector.

9. Materials and Methods a) Mice

Six- to 8-wk-old C57BL/6 mice were purchased from Harlan.

b) Cell Lines

The C57BL/6 syngeneic TC-1 tumor was immortalized with the HPV-16 E and E7 genes and transformed with the c-Ha-ras oncogene (25). TC-1 expresses low levels of E6 and E7 and is highly tumorigenic. TC-1 was grown in RPMI 1640, 10% FCS, 2 mM L-glutamine, 100 U/ml penicillin, 100 μg/ml streptomycin, 100 μM nonessential amino acids, 1 mM sodium pyruvate, 50 μM 2-MB, at 37° with 10% $CO_2$.

c) Production of Recombinant Adenoviruses

A transcription unit that included DNA encoding the signal peptide from the HGH gene upstream of DNA encoding the full length HPV type 16 E7 protein upstream of ΔCtΔTmCD40L was generated. DNA encoding the human growth hormone signal sequence MATGSRTSLLLAF-GLLCLPWLQEGSA (single letter amino acid code) (SEQ ID NO: 1) was prepared by annealing phosphorylated oligonucleotides (SEQ ID NOs:2 and 3) to generate the full 26 amino acid HGH sequence with Bgl II and NotI overhangs.

Growth Hormone Signal Upper Strand (Coding Sequence in Italics):

```
                                          (SEQ ID NO: 2)
5'-GATCT CCACC ATG GCT ACA GGC TCC CGG ACG TCC CTG
CTG CTG GCT TTT GGC CTG CTC TGC CTG CCC TGG CTT
CAA GAG GGC AGT GCC GGC-3'
```

Growth Hormone Signal Lower Strand:

```
                                          (SEQ ID NO: 3)
3'-A GGTGG TAC CGA TGT CCG AGG GCC TGC AGG GAC GAG
GAC CGA AAA CCG GAC GAG ACG GAC GGG ACC GAA GTT
CTC CCG TCA CGG CCGCCGG-5'.
```

Synthetic HGH signal sequence was prepared by annealing the above upper and lower strand oligos. The oligos were dissolved in 50 μl H₂O (about 3 mg/ml). 1 μl from each oligo (upper and lower stand) was added to 48 μl annealing buffer (100 mM potassium acetate, 30 mM HEPES-KOH pH 7.4, and 2 mM Mg-acetate) incubated at 4 minutes at 95° C., 10 minutes at 70° C. and slowly cooled to about 4° C. The annealed DNA was phosphorylated using T4 PNK (polynucleotide kinase) under standard conditions.

The HGH signal sequence with Bgl II and Not I overhangs was inserted via Bgl II and Not I into pShuttle-E7-ΔCtΔTmCD40L (no signal sequence) to yield pshuttle-HGH/E7-ΔCtΔTmCD40L.

pShuttle-E7-ΔCtΔTmCD40L (no signal sequence) was prepared as follows: Plasmid pDC406-mCD40L was purchased from the American Type Culture Collection. A pair of PCR primers (SEQ ID NOs: 4 and 5) was designed to amplify the mouse CD40 ligand from position 52 to 260 (i.e., without the cytoplasmic and transmembrane domains) and include sequence encoding a linker (indicated as "+ spacer") at the 5' end of the amplicon.

Mouse ΔCtΔTmCD40L+ Spacer Forward Primer (MCD40LSPF) (CD40L sequence italicized):

```
                                          (SEQ ID NO: 4)
5'-CCG CTCGAG AACGACGCACAAGCACCAAAATCAAAGGTCGAAGAG
GAAGTA-3'.
```

Mouse CD40L Reverse Primer (MCD40LR)
5'-CCC AAGCTT ATCAGAGTTTCACTAAGCCAA-3' (SEQ ID NO: 5)

The forward primer MCD40LSPF encoded a 10 residue spacer (FENDAQAPKS; single letter code; SEQ ID NO: 6) to be located between the tumor antigen and the CD40 ligand (mCD40L) of the transcription unit. PCR performed using the forward and reverse primers (SEQ ID NOs 4 and 5) and Plasmid pDC406-mCD40L as the template resulted in PCR fragment "space+ΔCtΔTMCD40L", which was inserted into the plasmid pShuttle-CMV (13) after restriction endonuclease digestion with Hind III (AAGCTT) and Xho I (CTCGAG). This vector is designated pShuttleΔCtΔTmCD40L. A vector was produced that was otherwise the same except that it encoded full length CD40L rather than the truncated form. This vector was made using a CD40 forward primer that annealed to the starting codons of murine CD40L This vector is designated pShuttleCD40L (no signal sequence).

Modification of pShuttleΔCtΔTmCD40L (no signal sequence) to include the HPV-16 E7 upstream of the CD40 ligand sequence was accomplished as follows: Sequence encoding the full HPV-16 E7 protein was obtained by PCR amplifying from the HPV viral genome using the following primers:

```
HPV 16 E7 forward primer (SEQ ID NO: 7)
5'-ATTT GCGGCCGC TGTAATCATGCATGGAGA-3'

HPV E7 reverse primer (SEQ ID NO: 8)
5-CC CTCGAG TTATGGTTTCTGAGAACAGAT-3'
```

The resulting amplicon was HPV 16 E 7 encoding DNA with 5' end Not 1 and 3' end Xho 1 restriction sites. The E7 DNA was inserted into the pShuttleΔCtΔTmCD40L between the CMV promoter and directly 5' to the spacer of the ΔCtΔTMCD40L sequence using Not I (GCGGCCGC) and Xho I (CTCGAG). The plasmid is designated pShuttle-E7-ΔCtΔTmCD40L (no signal sequence) and was used for insertion of the HGH signal sequence upstream of E7 to generate HGH/E7-ΔCtΔTmCD40L as already described. Thus, the transcription unit HGH/E7-ΔCtΔTmCD40L encodes the HGH secretory signal followed by the full length HPV type 16 E7 followed by a 10 amino acid linker with (FENDAQAPKS; SEQ ID NO: 9) followed by murine CD40 ligand residues 52-260.

A similar procedure as described above was used to insert the E7 encoding DNA upstream of full length CD40 in pShuttleCD40L (no signal sequence).

In a similar fashion, the green fluorescent protein (GFP) gene was inserted downstream of the CMV promoter and upstream the mΔCtΔTmCD40L or mCD40L (wildtype CD40L) and in a replication incompetent adenoviral vector. These vectors were used as controls. Other adenoviral vectors were created by inserting DNA encoding the HGH signal sequence between the CMV promoter and 5' to DNA encoding ΔCtΔTmCD40L or CD40L of vector pShuttle-ΔCtΔTmCD40L or pShuttleCD40L, respectively, to create vectors pShuttle-HGHΔCtΔTmCD40L and pShuttle-HGHCD40L, respectively.

A transcription unit that included DNA encoding the signal sequence of the mouse IgG kappa chain gene upstream of DNA encoding the full length HPV type 16 E7 protein ("K/E7") was generated by PCR using HPV16 plasmid and the following primers:

```
                                          (SEQ ID NO: 10)
5'-ACG ATG GAG ACA GAC ACA CTC CTG CTA TGG GTA CTG
CTG-3'

(SEQ ID NO: 11)
5'-TC CTG CTA TGG GTA CTG CTG CTC TGG GTT CCA GGT
TC-3'

(SEQ ID NO: 12)
5'-TG CTG TGG GTT CCA GGT TCC ACT GGT GAC ATG CAT
G-3';

(SEQ ID NO: 13)
5'-TGG GTT CCA GGT TCC ACT GGT GAC ATG CAT GGA GAT
ACA CCT AC-3'; and (SEQ ID NO: 14)
5'-CCG CTC GAG TGG TTT CTG AGA ACA GAT GGG GCA C-3.'
```

K/E7 with the upstream kappa signal sequence was generated by four rounds of PCR amplification (1st round: primers 4+5; 2nd round: add primer 3; 3rd round: add primer 2; 4th round: add primer 1). The K/E7 encoding DNA was cloned into the pcDNA™ 3.1 TOPO vector (Invitrogen, San Diego, Calif.) forming pcDNA-K/E7.

A DNA fragment that contained the mouse CD40 ligand from which the transmembrane and cytoplasmic domain had been deleted (ΔCtΔTmCD40L) was generated from a mouse CD40 ligand cDNA Plasmid (pDC406-mCD40L; ATCC) using the following PCR primers:

(SEQ ID NO: 15)
5'-CCG CTCGAG AAC GAC GCA CAA GCA CCA AAA AGC AAG

GTC GAA GAG GAA GTA AAC CTT C-3';
and (SEQ ID NO: 16)
5'-CGCGCCGCGCGCTAG *TCTAGA* GAGTTTGAGTAAGCCAAAAGATGA G-3' (high fidelity PCR kit, Roche).

Fragment ΔCtΔTmCD40L was digested with Xba I and XhoI restriction endonucleases and then ligated into pcDNA-E7. K/E7-ΔCtΔTmCD40L fragment was cut from the pcDNA vector and inserted into the pShuttle plasmid using Hind III and Xba I sites (pShuttle K/E7-CtΔTmCD40L). Thus, the K/E7-ΔCtΔTmCD40L fragment includes the kappa chain secretory signal followed by the fall length HPV type 16 E7 followed by a 10 amino acid linker (LQNDAQAPKS; SEQ ID NO: 17) followed by murine CD40 ligand residues 52-260.

Adenoviral vector encoding a fusion protein with E7 upstream of full length mouse CD40L was made using primers to amplify full length mouse CD40L. The following primers were used:

(SEQ ID NO: 18)
5'-GAGAC CTC GAG CAGTCA GC ATGATAGA AACATACAGCCAAC

CTTCCC-3';

(SEQ ID NO: 19)
5'-CCGCGC CCCAAGCTTA TCAGAGTTTGAGTAAGCCAAAAG-3'.

Figure 2A:
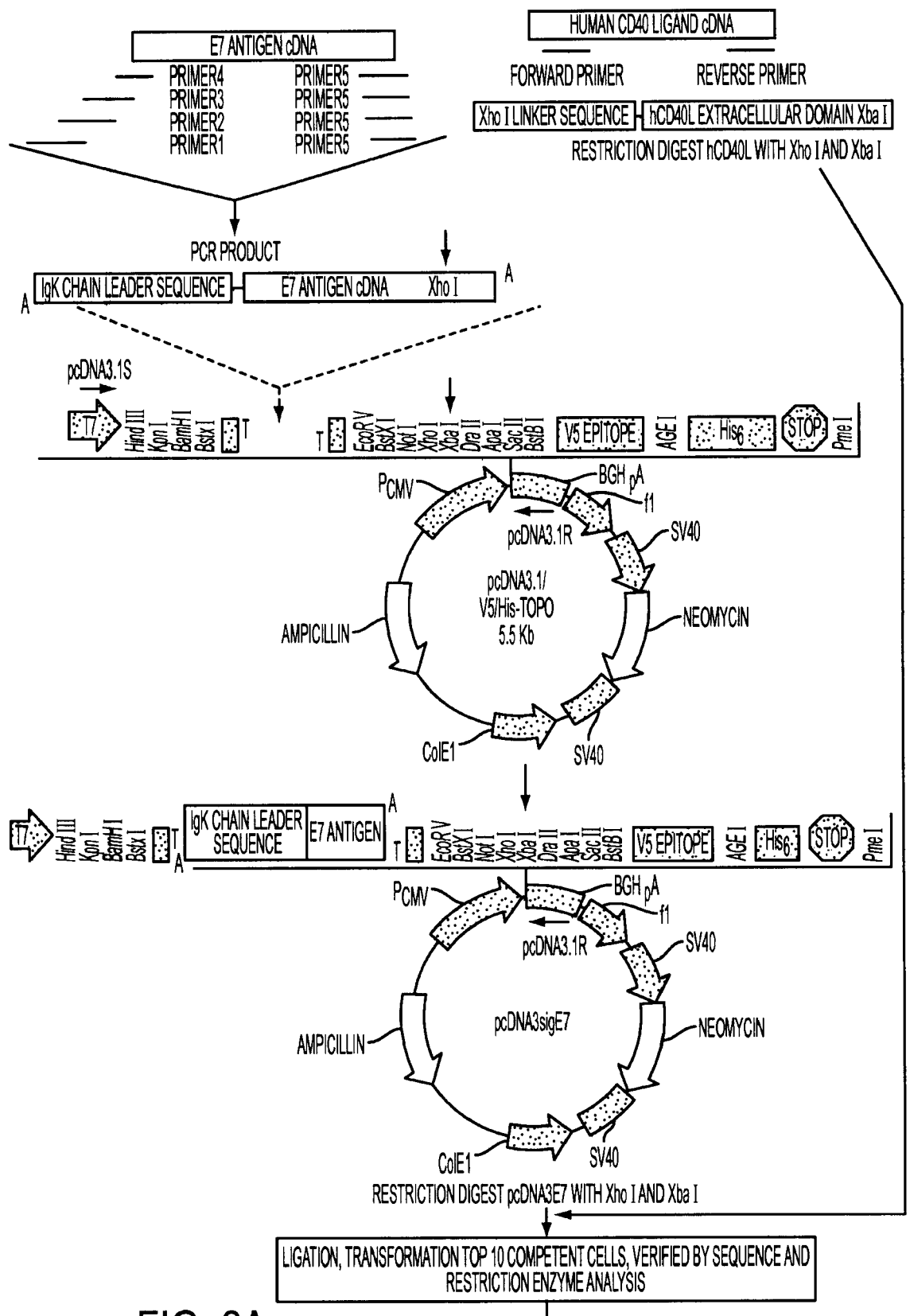
FIGS. 2A and 2B show a scheme for constructing adenoviral expression vector encoding E7-ΔCtΔTmCD40L.
Figure 2B:
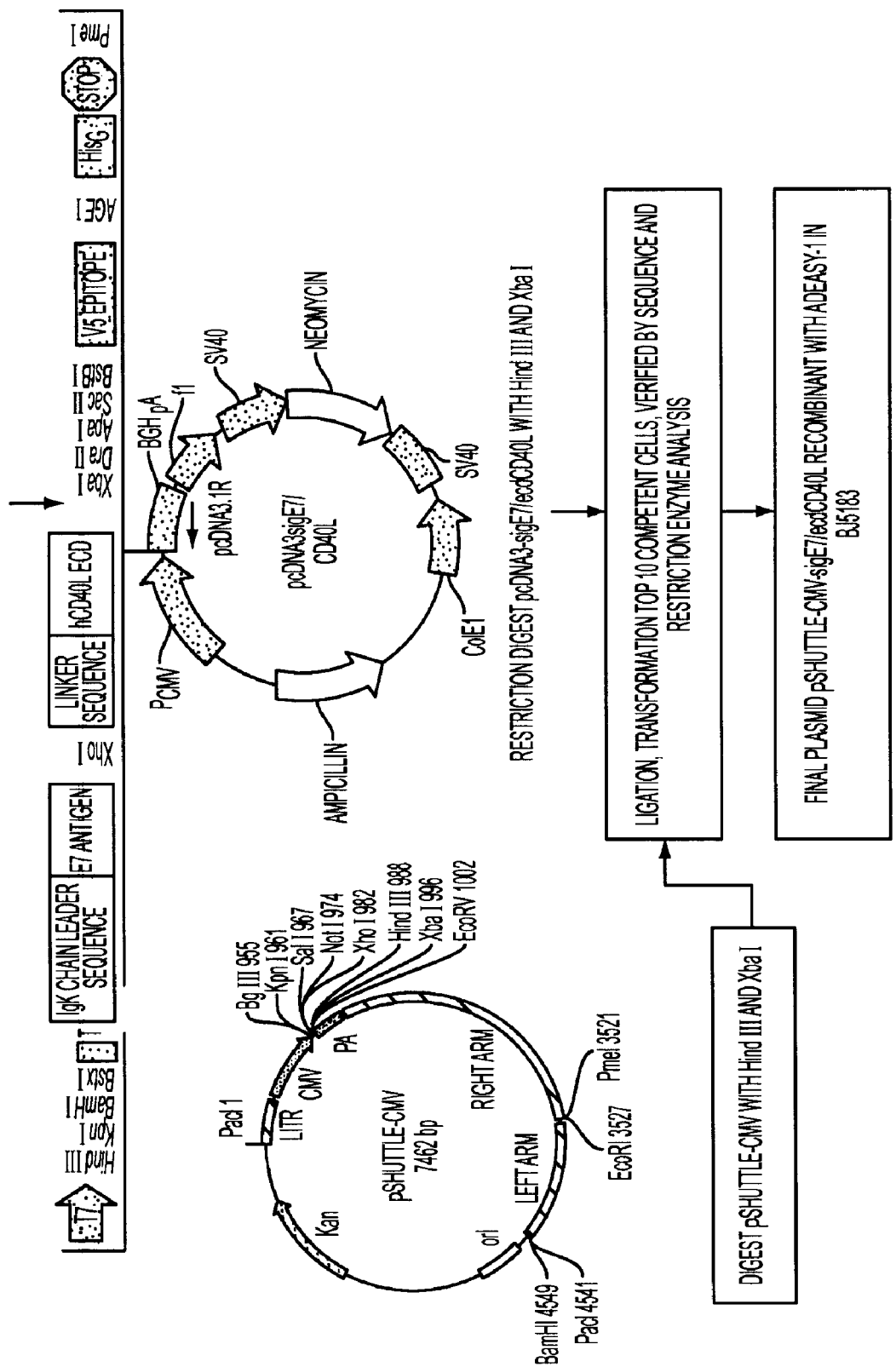

Amplified DNA was initially subcloned into the pcDNA3 with Xba I and XhoI restriction endonucleases. The full length CD40L gene or ΔCtΔTmCD40L was directionally cloned into the pShuttle plasmid with the Hind III and Xba I sites. An overview of the scheme for constructing adenoviral expression vector encoding E7-ΔCtΔTmCD40L is shown in FIGS. 2A. and 2B.

The recombinant adenoviral vectors were generated using the Adasy vector system (Strategene, San Diego, Calif.). Briefly the resulting plasmid pShuttle-HGH/E7-ΔCtΔTmCD401, pShuttle-HGH/CD40L, pShuttle-HGH/E7-CD40L, pShuttle-HGH/GFP, pShuttleHGH/GFP-CD40L, and pShuttle-HGH/E7 were linearized with Pme I and co-transformed into *E. coli* strain BJ5183 together with pAdEasy-1, the viral DNA plasmid. Recombinants were selected with kanamycin and screened by restriction enzyme analysis. The recombinant adenoviral construct was then cleaved with Pac I to expose its Inverted Terminal Repeats ITR) and transfected into 293A cells to produce viral particles. The titer of recombinant adenovirus was decided by Tissue culture Infectious Dose (TCID$_{50}$) method.

Primers for amplifying human ΔCtΔTMCD40L+ spacer using a human CD40 ligand cDNA template are set forth below.

Human ΔCtΔTmCD40L+ Spacer Forward Primer (HCD40LSPF) (CD40L sequence italicized):

(SEQ ID NO: 20)
5'-CCG CTCGAGAACGACGCACAAGCACCAAAATCA*CATAGAAGGTTGG*

*ACAAG*-3'.

Human CD40L reverse primer (HCD40LR)
(SEQ ID NO: 21)
5'-CCC AAGCTT TCAGAGTTTGAGTAAGCCAAAGGAC-3'

These primers will amplify a ΔCtΔTmCD40L+ spacer which encodes 47-261 of human CD40L. The forward primer HCD40LSPF encodes a 10 residue spacer (JEDAQAPKS; single letter code; SEQ ID NO: 9) to be located between the tumor antigen and the CD40 ligand (hCD40L) of the transcription unit. PCR performed using the forward and reverse primers (SEQ ID NOs 20 and 21) and Plasmid pDC406-hCD40L as the template results in PCR fragment "space+ΔCtΔTmCD40L (human)", which is inserted into the plasmid pShuttle-CMV (13) after restriction endonuclease digestion with Hind III (AAGCTT) and Xho I (CTCGAG). This vector is designated pShuttleΔCtΔTmCD40L (human). Modification of pShuttleΔCtΔTmCD40L (human) to include the HPV-16 E7 upstream of the human CD40 ligand sequence was accomplished essentially as described above for the murine CD40 ligand encoding vectors. The resulting plasmid is designated pShuttle-E7-ΔCtΔTmCD40L (human)(no signal sequence) and is used for insertion of the HGH signal sequence upstream of E7 to generate HGH/E7-ΔCtΔTmCD40L (human). Thus, the transcription unit HGH/E7-ΔCtΔTmCD40L (human) encodes the HGH secretory signal followed by the full length HPV type 16 E7 followed by a 10 amino acid linker (FENDAQAPKS; SEQ ID NO:9) followed by human CD40 ligand residues 47-261.

d) In Vitro Expression of Adenoviral Vector Transcription Units

The coupled in vitro transcription-translation system of RILL (TNT kits from Protégé Corp.) was used for the synthesis of the following vectors: Ad-E7-CtΔTmCD40L, Ad-E7-wtTmCD40L, Ad-ΔCtΔTmCD40L, Ad-wtTmCD40L, and Ad-E7. Two µg of each plasmid DNA or PCR generated template DNA was added to the 50 µl reaction mixture containing 25 µl of RRL, 2 µL of TNT reaction buffer, 1 µl of T7 RNA polymerase, 1 µl of amino acid mixture (1 mM) without methionine, 4 µl of [$^{35}$S]-methionine, and 1 µl of ribonuclease inhibitor RNAsin (40 U/µl). The reaction was completed by incubation at 30° C. for 1 hr. 15 ul of each [$^{35}$S]-labeled product was run on a 10% SDS-PAGE gel and exposed to X-film overnight.

e) Western blot Analysis

The cell lysate derived from 293 cells infected by an adenoviral vector at MOI 40 was fractionated on a 10% reducing SDS-PAGE gel and transferred to an IMMOBILON-P membrane (Millipore, Bedford, Mass.). After blocking with 5% nonfat milk for 2 h at room temperature, the membrane was probed with an antibody against the specific mouse CD40 ligand (mCD40L) in TBS-T buffer (20 mM Tris-HCl [pH 7.6], 137 mM NaCl, and 0.5% Tween 20) in the presence of 2% BSA overnight. After washing four times with TBS-T buffer, the blot was incubated with goat anti-hamster alkaline phosphatase conjugated antibody (Jackson Immunoresearch) for 1 hour. The immunoreactive bands were visualized on membrane by using the ProtoBlot II AP system (Promega Corp.).

f) Flow Cytometry Analyses of DC

To quantify the expression level of surface molecules of APCs or DCs, the test cells were stained with FITC- or PE-conjugated anti-mouse monoclonal antibodies (mAbs) for CD80, CD54, and CD11c (Pharmingen), for 30 min on ice, prior to immunostaining with labeled Abs. The APCs were first incubated with a Fc-γ blocking antibody (anti-mouse CD16/CD32 antibody) to avoid the nonspecific binding of mAbs to Fc-γ receptors. The cells were then washed twice, fixed in 4% paraformaldehyde, and analyzed using a Becton Dickinson flow cytometer (BD FACS Calipur™).

g) Cytokine Production of Ad-mCD40-Modified DCs

The DCs were infected with the following adenoviral vectors: Ad E7-ΔCtΔTmCD40L, AdmCD40L, AdE7-CD40L, AdGFP, AdGFP-mCD40L, AdE7 or phosphate-buffered saline (PBS) at MOI 100, and plated in 24-well plates at $2\times10^5$ cells/ml. After incubation for 24 hours at 37° C., the supernatant fluid (1 ml) was harvested and centrifuged to remove debris. The level of murine IL-12 or IFN-gamma released into the culture medium was assessed by enzyme-linked immunosorbent assay ELISA), using the mouse IL-12 p70 or IFN-gamma R & D Systems respectively.

h) DC Migration Assays

The protocol used to study the in vitro migration of DCs was the same as that used by Romani et al (21). In brief, the skin of the ear of mice was split in dorsal and ventral halves and dorsal halves were cultured on the bottom membrane of the inner chamber of six well double-chamber tissue culture plate (transwell no 3414, Costar). The outer chamber was loaded with $1\times10^8$ vector particles. It was then filled with culture medium so that the vector particles could bath the skin from underneath. The epidermal part of the skin was thus exposed to air. The cultures were incubated at 37° C. for 3 days. The number of DCs that had emigrated from the skin into culture medium was counted under the hemocytometer.

The DC in vivo migration experiment was carried out as follows. After the bone marrow derived DCs were cultured 6 days with IL-3, GM-CSF, they were loaded with the CFDA SE suprevital dye. Briefly, the DCs were incubated with 10 ul of CFDA SE for 15 min at 37° C. The dendritic cells were then pelleted and resuspended in fresh prewarmed medium for 30 min. The cells were mixed with each recombinant adenoviral vector at MOI 200. The vector was then injected into the left flank of the test mouse. Three days later, the axillary lymph nodes draining the region of the injection site for the DCs were removed, frozen tissue sections made and observed in the immunofluorescence microscope.

i) Immunohistochemical Staining

Vaccinated mice were sacrificed 3 days after the Ad E7-ΔCtΔTmCD40L, Ad-ΔCtΔTmCD40L, AdE7-CD40L, AdE7-CD40L vector vaccination. The skin at the site of vector subcutaneous injection was biopsied, embedded in Oct solution, and cut into 5-μm sections. The slides were incubated with rat anti-MHC-II antibody, rat anti-CD40L antibody, and rat anti-CD80 polyclonal Ab (Bioscience). This was followed by exposure to biotinylated goat anti-rat IgG antibody (1:200 dilution) and avidin-biotin complex (1:100 dilution; Vector, Burlingame, Calif.). The stained slides then were mounted, and studied under a fluorescence microscope.

j) Cytokine Profile by ELISPOT Assays

The presence of E7-specific effector T cells in the immunized mice was also assessed in ELISPOT assays, as previously described (26, 27). Briefly, splenocytes obtained from mice vaccinated with each of the different vectors were restimulated in vitro by culture with the TC-1 cell line (responder-to-stimulator ratio 25:1) in the presence of 10 U/ml IL-2 for 48 hours. Re-stimulated splenocytes were then plated in 96-well nitrocellulose filter plates ($5\times10^4$ cells in 100 microliters). The wells were precoated with rat anti-mouse anti-IFN-antibody or anti-IL-4 antibody. After incubation for 24 hours at 37° C./5% $CO_2$, the plates were then washed with PBS, and the presence of cytokine-producing spleen cells was detected by incubation at 4° C. with biotinylated goat anti-rat secondary antibody, followed by 100 microliter/well horseradish peroxidase avidinD and 150 microliter/well freshly prepared substrate buffer (0.4 mg/ml 3-amino-9-ethyl-carbazole in a total of 50 ml 0.05 mol/L sodium acetate buffer) and 20 microliter 30% $H_2O_2$. The stained spots corresponding with IFN producing cells or IL-4 producing cells were enumerated under a dissecting microscope.

k) Cytotoxicity Assay

For these studies, mice received vaccination via a subcutaneous injection of the following vectors: Ad-E7-ΔCtΔTmCD40L (secretable CD40 ligand), Ad-ΔCtΔTmCD40L (secretable CD40 ligand), Ad-E7-CD40L (non-secretable CD40L), Ad-CD40L (non-secretable ligand) and Ad-E7. The vectors were injected on days 0 and 7 as a subcutaneous injection. As a control, PBS was injected subcutaneously on days 0 and 7 (control mice). Mononuclear cells from the spleens of these mice (vector injected or PBS injected) were used as the source of effector cells for cytotoxicity studies. Aliquots of the spleen cell suspensions were then co-incubated with mitomycin C-treated TC-1 cells in RPMI 1640 medium, supplemented with 10% FBS, 50 M 2-mercaptoethanol, 2 mM glutamine, 1 mM pyruvate, and nonessential amino acids, under cell culture conditions for 5 days. To perform the cytotoxicity assay, $5\times10^3$ of TC-1 tumor cells (target cells) were incubated with the stimulated splenic mononuclear cells (effector cells) at an effector/target ratio of 100:1 for 4 hours at 37° C., in culture media containing 5% FBS. At the end of the incubation, mononuclear cell-mediated cytotoxicity was determined using the nonradioactive cytotoxicity assay kit. Released LDH in culture supernatants was measured by an ELISA plate reader. The data were calculated as:

% CYTOTOXICITY=(EXR ESR TSR+CMB/TMR TSR VC+CMB) 100 where EXR is experimental LDH release, ESR is effector cell spontaneous LDH release, TSR is target cell spontaneous LDH release, TMR is target cell maximum LDH release, VC is volume correction, and CMB is culture medium LDH back-ground. Statistics: Student's unpaired t-test was used to determine the differences between the various groups in the proliferation and cytotoxicity assays. Statistical significance was determined at the 0.01 level.

l) In vivo Efficacy Experiment in Mouse Model

Mice (5 or 10 per group) were vaccinated via subcutaneous injection with $1\times10^8$ PFU Ad-E7-ΔCtΔTmCD40L, Ad-E7, Ad-E7-CD40L, Ad-ΔCtΔTmCD40L or Ad-CD40L vectors. One week later, mice were boosted with the same adenoviral vector regimen as the first vaccination. One week after the last vaccination, mice were to challenged by subcutaneous injection of $5\times10^5$ TC-1 cells/mouse in the right leg and then monitored twice a week.

The donor splenocytes were harvested from tumor-free donor C57BL/6 mice and passed over magnetic columns to enrich for total T cells. Tumor growth was measured as described previously.

m) Statistics

All parameters were analyzed using Students t test, or ANOVA® followed by Scheffé's procedure for multiple comparisons as post-hoc analysis; all data shown is presented as mean ±S.E. of the mean (S.E.).

11. References

1. Shortman K, and Caux C. Dendritic cell development: multiple pathways to nature's adjuvants Stem Cells 15:409-419, 1997.
2. Steinbrink K, Graulich E, Kubsch S, Knop J, Enk A H. CD4(+) and CD8(+) anergic T cells induced by interleukin-10-treated human dendritic cells display antigen-specific suppressor activity. Blood 99: 2468-2476, 2002.
3. Kusuhara M, Matsue K, Edelbaum D, Loftus J, Takashima A, Matsue H. Killing of naive T cells by CD95L-transfected dendritic cells (DC): in vivo study using killer DC-DC hybrids and CD4(+) T cells from DO11.10 mice. Eur J Immunol 32:1035-1043, 2002.
4. Gunzer M, Janich S, Varga G, Grabbe S. Dendritic cells and tumor immunity. Semin Immunol 13:291-302, 2001.
5. Luft T, Luetjens P, Hochrein H, Toy T, Masterman K A, Rizkalla M, Maliszewski C, Shortman K, Cebon J, and Maraskovsky E. IFN-alpha enhances CD40 ligand-mediated activation of immature monocyte-derived dendritic cells. Int Immunol 14:367-380, 2002.
6. Skov S, Bonyhadi M, Odum N, and Ledbetter J A. IL-2 and IL-15 regulate CD154 expression on activated CD4 T cells J. Immunol. 164: 3500-3505, 2000.
7. Paglia P, et al. Murine dendritic cells loaded in vitro with soluble protein prime cytotoxic T lymphocytes against tumor antigen in vivo (see comments). J Exp Med 183: 317-322, 1996.
8. Zitvogel L, et al. Therapy of murine tumors with tumor peptide-pulsed dendritic cells: dependence on T cells, B7 co-stimulation, and T helper cell 1-associated cytokines. J Exp Med. 183: 87-97, 1996.
9. Fong L, et al. Dendritic cells injected via different routes induce immunity in cancer patients. J. Immunol. 166: 4254-4259, 2001.
10. Markowicz S, Engleman E G. Granulocyte-macrophage colony-stimulating factor promotes differentiation and survival of human peripheral blood dendritic cells in vitro. J Clin Invest 85: 955-961, 1990.
11. Hsu F J, et al. Vaccination of patients with B-cell lymphoma using autologous antigen-pulsed dendritic cells. Nat. Med. 2: 52-58, 1996.
12. Nestle F O, et al. Vaccination of melanoma patients with peptide- or tumor lysate-pulsed dendritic cells. Nat. Med. 4: 328-332, 1998.
13. Murphy G P, et al. Infusion of dendritic cells pulsed with HLA-2A2-specific prostate-specific membrane antigen peptides: a phase II prostate cancer vaccine trial involving patients with hormone-refractory metastatic disease. Prostate 38: 73-78, 1999.
14. Dhodapkar M V, et al. Rapid generation of broad T-cell immunity in humans after a single injection of mature dendritic cells. J Clin Invest. 104: 173-180, 1999.
15. Zwaveling S, Ferreira Mota S C, Nouta J, Johnson M, Lipford G B, Offringa R, van der Burg S H, and Melief C J. Established human papillomavirus type 16-expressing tumors are effectively eradicated following vaccination with long peptides J Immunol 350-358, 2002.
16. Liu W, Gao F, Zhao K, Zhao W, Fernando G, Thomas R, and Frazer I. Codon Modified Human Papillomavirus Type 16 E7 DNA Vaccine Enhances Cytotoxic T-Lymphocyte Induction and Anti-tumor Activity. Virology 15: 301-343, 2002.
17. Lamikanra A, Pan Z K, Isaacs S N, Wu T C, and Paterson Y. Regression of established human papillomavirus type 16 (HPV-16) immortalized tumors in vivo by vaccinia viruses expressing different forms of HPV-16 E7 correlates with enhanced CD8(+) T-cell responses that home to the tumor site. J Virol: 9654-9664, 2001.
18. Stanley M A. Human papillomavirus vaccines. Curr Opin Mol. Ther. 4:15-22, 2002.
19. Rudolf M P, Fausch S C, Da Silva D M, Kast W M. Human dendritic cells are activated by chimeric human papillomavirus type-16 virus-like particles and induce epitope-specific human T cell responses in vitro. J. Immunol. 166: 5917-5924, 2001.
20. Bell D, Young J W, Banchereau J. Dendritic cells. Adv Immunol. 72: 255-324, 1999.
21. Timmerman J M, Levy P Dendritic cell vaccines for cancer immunotherapy. Annual Rev Med. 50: 507-529, 1999.
22. Palucka K, Banchereau J. Dendritic cells: a link between innate and adaptive immunity. J Clin Immunol. 19:12-25, 1999.
23. Ribas A, Butterfield L H, Amamani S N, Dissette V B, Kim D, Meng W S, Miranda G A, Wang H J, McBride W H, Glaspy J A, and Economou J S. CD40 cross-linking bypasses the absolute requirement for CD4 T cells during immunization with melanoma antigen gene-modified dendritic cells. Cancer Res. 61:8787-8793, 2001.
24. Broder H, Anderson A, Odesa S K, Kermen T, and Liau L M. Recombinant adenovirus-transduced dendritic cell immunization in a murine model of central nervous system tumor Neurosurg Focus 9:1-8, 2000.
25. Crook T, Morgenstern J P, Crawford L and Banks L. Continued expression of HPV-16 E7 protein is required for maintenance of the transformed phenotype of cells co-transformed by HPV-16 plus EJ-ras. EMBO J. 8: 513-519, 1989.
26. Larsson M, Jin X, Ramratnam B, Ogg G S, Engelmayer J, Demoitie M A, McMichael A J, Cox W I Steinman R M, Nixon D, and Bhardwaj N. A recombinant vaccinia virus based ELISPOT assay detects high frequencies of Pol-specific CD8 T cells in HIV-1-positive individuals AIDS 13:767-777, 1999.
27. Rininsland F H, Helms T, Asaad R J, Boehm B O, and Tary-Lehmann M. Granzyme B ELISPOT assay for ex vivo measurements of T cell immunity J Immunol Methods 240:143-155, 2000.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the a and that such modifications and variations are considered to be within the scope of this invention as defined by the appended claims.

Other embodiments are set forth within the following claims.

We claim:

1. An adenoviral expression vector for generating immunity against a tumor antigen, said vector comprising a transcription unit encoding a polypeptide, said polypeptide comprising from the amino terminus a secretory signal sequence, a tumor antigen, and a CD40 ligand, wherein said tumor antigen is different from said CD40 ligand and wherein said CD40 ligand is missing all or substantially all of the transmembrane domain rendering the CD40 ligand secretable, and wherein said polypeptide is adapted to promote Class I MHC restricted cytotoxic T cell lymphocytes (CTLs).

2. The adenoviral expression vector of claim 1 wherein said tumor antigen is a human tumor antigen, and where said tumor antigen is connected to the amino terminus of said CD40 ligand rendered secretable and adapted to promote presentation of the tumor antigen on Class I MHC of human dendritic cells.

3. The adenoviral expression vector of claim 2 wherein said tumor antigen is the E7 protein of human papilloma virus.

4. The adenoviral expression vector of claim 1 wherein said transcription unit encodes a linker between said tumor antigen and the amino terminus of said CD40 ligand leaving the carboxyl terminus of CD40 ligand free to directly bind to a CD40 on dendritic cells.

5. The adenoviral expression vector of claim 1 wherein said vector includes a human cytomegalovirus promoter/enhancer for controlling transcription of the transcription unit.

6. The adenoviral expression vector of claim 1 wherein said tumor antigen is a human tumor antigen, and where the molecular weight of the tumor antigen is selected such that the molecular weight of the tumor antigen is small enough so as not to disrupt the trimeric structure of the CD40 ligand.

7. The adenoviral expression vector of claim 1 wherein said CD40 ligand lacks a cytoplasmic domain.

8. The adenoviral expression vector of claim 1 wherein the vector encodes a CD40 ligand that includes no more than six residues from either end of the transmembrane domain, and wherein said vector does not encode the transmembrane domain of the CD40 ligand.

9. The adenoviral expression vector of claim 1 wherein said polypeptide is further adapted to stimulate a Th1 immune response.

10. The adenoviral expression vector of claim 6 wherein said CD40 ligand comprises the amino acid residues 47-261, the extracellular domain of CD40 ligand.

11. The adenoviral expression vector of claim 6 wherein said CD40 ligand comprises the amino acid residues 1-22, the cytoplasmic domain of CD40 ligand, and the amino acid residues 47-261, the extracellular domain of CD40 ligand.

12. The adenoviral expression vector of claim 1 wherein said vector is rendered non-replicating in normal human cells.

13. A method of generating an immune response in an individual against cells expressing a tumor antigen, comprising administering to the individual an effective amount of the adenoviral expression vector of claim 1.

14. The method of claim 13 wherein said tumor antigen is the E7 protein of human papilloma virus.

15. The method of claim 13 wherein said CD40 ligand is human CD40 ligand.

16. The method of claim 13 wherein said cancer cells are cervical cancer cells.

17. The method of claim 16 wherein said tumor antigen is E7 protein of human papilloma virus.

18. The method of claim 13 wherein said administering is repeated.

19. The method of claim 13 wherein said immune response includes the generation of cytotoxic CD8$^+$ T cells against said tumor associated antigen.

20. The method of claim 13 wherein following administration, said vector is taken up by cells which subsequently secrete a fusion protein encoded by the transcription unit.

21. The method of claim 20 wherein said fusion protein forms a homotrimer through interaction of CD40 ligand extracellular domains.

22. A method of treating an individual with cancer that expresses a tumor antigen, comprising administering to the individual an effective amount of the adenoviral expression vector of claim 1.

23. The method of claim 22 wherein said tumor antigen is the E7 protein of human papilloma virus.

24. The method of claim 22 wherein said CD40 ligand is human CD40 ligand.

25. The method of claim 22 wherein said cancer is cervical cancer.

26. The method of claim 25 wherein said tumor antigen is E7 protein of human papilloma virus.

27. The method of claim 22 wherein said administering is repeated.

28. The method of claim 22 wherein said immune response includes the generation of cytotoxic CD8$^+$ T cells against said tumor associated antigen.

29. The method of claim 22 wherein following administration, said vector is taken up by cells which subsequently secrete a fusion protein encoded by the transcription unit.

30. The method of claim 29 wherein said fusion protein forms a homotrimer through interaction of CD40 ligand extracellular domains.

31. A method of generating immunity in a subject to infection by human papilloma virus, comprising administering to the individual an effective amount of the adenoviral expression vector of claim 1 wherein said tumor antigen is the E6 or E7 protein of human papilloma virus.

32. The method of claim 31 wherein said CD40 ligand is human CD40 ligand.

33. The method of claim 31 wherein said administering is repeated.

34. The method of claim 31 wherein said immune response includes the generation of cytotoxic CD8$^+$ T cells against human papilloma virus.

35. The adenoviral expression vector of claim 2, wherein said tumor antigen includes a tumor associated antigen.

36. The adenoviral expression vector of claim 35, wherein said tumor antigen additionally includes a tumor specific antigen.

37. The adenoviral expression vector of claim 1, whereby in generating an immune response against a human tumor antigen, the tumor antigen/CD40 ligand is encoded to cause human dendritic cells to present tumor antigens on Class I MHC in order to induce activation and amplification of cytotoxic CD8+ effector T cells against the tumor antigen.

38. The adenoviral expression vector of claim 3, whereby the tumor antigen is a tumor associated antigen.

39. The adenoviral expression vector of claim 1 wherein said tumor antigen is a human tumor antigen and the adenoviral vector is adapted to cause human cells infected by the vector to manufacture quantities of tumor antigen/CD40 ligand fusion proteins sufficient to induce an immune response wherein said antigen/CD40 ligand fusion protein binds to CD40 on dendritic cells causing dendritic cells to be activated and to migrate to lymph nodes to activate and amplify CD8+ effector T cells to kill cancer cells which are positive for said tumor antigen.

40. An adenoviral expression vector for generating immunity against a tumor antigen, said vector comprising a transcription unit encoding a fusion protein adapted to promote a Class I MHC restricted CTLs, the fusion protein comprising from the amino terminus a secretory signal sequence, a tumor antigen and a CD40 ligand, wherein said tumor antigen is different from the CD40 ligand and where the CD40 ligand is missing all or substantially all of the transmembrane domain rendering the CD40 ligand secretable, said vector adapted to cause secretion of quantities of tumor antigen/CD40 ligand fusion proteins sufficient to induce a restricted cellular immune response, said CD40 ligand adapted to bind to CD40 on dendritic cells leading to dendritic cell activation and presentation of tumor antigens on Class I MHC of the dendritic cells and migration of the dendritic cells to lymph nodes to induce the amplification of antigen specific CD8+ effector T cells leading to killing of cancer cells positive for the tumor antigen.

41. The adenoviral expression vector of claim 40 where the activated dendritic cells are tumor antigen-loaded antigen presenting cells.

42. The adenoviral expression vector of claim 40 where the dendritic cells are activated for migration to lymph nodes to induce an antigen specific cellular immune response that kills tumor cells.

43. The adenoviral expression vector of claim 40 including a linker molecule between the tumor antigen and the CD40 ligand and where a combined tumor antigen molecular weight and linker molecular weight is minimized to better stabilize the fusion protein and to enhance the binding properties of the CD40 ligand with a CD40 on dendritic cells.

44. The adenoviral expression vector of claim 40 where said adenoviral vector is adapted to promote amplification of a Class I MHC restricted CTLs through subcutaneous injection by infection of most individual cells at the site of injection driving a continuous release of quantities of the tumor antigen/CD40 ligand secretory fusion protein sufficient to induce a robust immune response.

45. The adenoviral expression vector of claim 44 where the continuous release is adapted to last at least for a period of ten days enabling a robust immune response.

46. The adenoviral expression vector of claim 40 where the immunity generated in an individual has the ability to promote long term systemic immunity memory in individual cell lines carrying the tumor antigen.

47. The viral expression vector of claim 46 where the memory is capable to extend for a period of at least one year.

48. The adenoviral expression vector of claim 40 wherein said transcription unit is incorporated into a E1 gene region of the adenoviral expression vector.

49. The adenoviral expression vector of claim 40 wherein the CD40 ligand is the native CD40 ligand version adapted to directly bind to a receptor on dendritic cells.

50. The adenoviral expression vector of claim 40 and wherein said fusion protein is further adapted to stimulate a Th1 immune response.

* * * * *

UNITED STATES PATENT AND TRADEMARK OFFICE
CERTIFICATE OF CORRECTION

| | | |
|---|---|---|
| PATENT NO. | : 8,119,117 B2 | Page 1 of 1 |
| APPLICATION NO. | : 10/534605 | |
| DATED | : February 21, 2012 | |
| INVENTOR(S) | : Deisseroth et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1158 days.

At column 18, line 14, change the term "JEDAQAPKS" to "FENDAQAPKS".

In claim 8, line 2 (at column 29, line 64), change the word "a" to "the".

Signed and Sealed this
Seventh Day of August, 2012

David J. Kappos
*Director of the United States Patent and Trademark Office*

SEQUENCE LISTING

<160> NUMBER OF SEQ ID NOS: 21

<210> SEQ ID NO 1
<211> LENGTH: 26
<212> TYPE: PRT
<213> ORGANISM: Artificial Sequence
<220> FEATURE:
<223> OTHER INFORMATION: Synthetic Construct

<400> SEQUENCE: 1

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 2
<211> LENGTH: 91
<212> TYPE: DNA
<213> ORGANISM: Artificial Sequence
<220> FEATURE:
<223> OTHER INFORMATION: Growth hormone signal upper strand

<400> SEQUENCE: 2
gatctccacc atggctacag gctcccggac gtccctgctc ctggcttttg gcctgctctg      60
cctgccctgg cttcaagagg gcagtgccgg c                                    91

<210> SEQ ID NO 3
<211> LENGTH: 91
<212> TYPE: DNA
<213> ORGANISM: Artificial Sequence
<220> FEATURE:
<223> OTHER INFORMATION: Growth Hormone Signal Lower Strand

<400> SEQUENCE: 3
aggtggtacc gatgtccgag ggcctgcagg gacgaggacc gaaaaccgga cgagacggac      60
gggaccgaag ttctcccgtc acggccgccg g                                    91

<210> SEQ ID NO 4
<211> LENGTH: 51
<212> TYPE: DNA
<213> ORGANISM: Artificial Sequence
<220> FEATURE:
<223> OTHER INFORMATION: Mouse ?Ct?TmCD40L+ Spacer Forward Primer
      (MCD40LSPF)

<400> SEQUENCE: 4
ccgctcgaga acgacgcaca agcaccaaaa tcaaaggtcg aagaggaagt a               51

<210> SEQ ID NO 5
<211> LENGTH: 30
<212> TYPE: DNA
<213> ORGANISM: Artificial Sequence
<220> FEATURE:
<223> OTHER INFORMATION: Mouse CD40L reverse primer (MCD40LR)

<400> SEQUENCE: 5
cccaagctta tcagagtttc actaagccaa                                      30

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 6

Phe Glu Asn Asp Ala Gln Ala Pro Lys Ser
1               5                   10

<210> SEQ ID NO 7
<211> LENGTH: 30
<212> TYPE: DNA
<213> ORGANISM: Artificial Sequence
<220> FEATURE:
<223> OTHER INFORMATION: HPV 16 E7 forward primer

<400> SEQUENCE: 7
atttgcggcc gctgtaatca tgcatggaga                                  30

<210> SEQ ID NO 8
<211> LENGTH: 29
<212> TYPE: DNA
<213> ORGANISM: Artificial Sequence
<220> FEATURE:
<223> OTHER INFORMATION: HPV E7 reverse primer

<400> SEQUENCE: 8
ccctcgagtt atggtttctg agaacagat                                   29

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Phe Glu Asn Asp Ala Gln Ala Pro Lys Ser
1               5                   10

<210> SEQ ID NO 10
<211> LENGTH: 39
<212> TYPE: DNA
<213> ORGANISM: Artificial Sequence
<220> FEATURE:
<223> OTHER INFORMATION: Primer

<400> SEQUENCE: 10
acgatggaga cagacacact cctgctatgg gtactgctg                        39

<210> SEQ ID NO 11
<211> LENGTH: 37
<212> TYPE: DNA
<213> ORGANISM: Artificial Sequence
<220> FEATURE:
<223> OTHER INFORMATION: Primer

<400> SEQUENCE: 11
tcctgctatg ggtactgctg ctctgggttc caggttc                          37

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
tgctctgggt tccaggttcc actggtgaca tgcatg                           36
```

```
<210> SEQ ID NO 13
<211> LENGTH: 44
<212> TYPE: DNA
<213> ORGANISM: Artificial Sequence
<220> FEATURE:
<223> OTHER INFORMATION: Primer

<400> SEQUENCE: 13
tgggttccag gttccactgg tgacatgcat ggagatacac ctac            44

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
ccgctcgagt ggtttctgag aacagatggg gcac                        34

<210> SEQ ID NO 15
<211> LENGTH: 58
<212> TYPE: DNA
<213> ORGANISM: Artificial Sequence
<220> FEATURE:
<223> OTHER INFORMATION: Primer

<400> SEQUENCE: 15
ccgctcgaga acgacgcaca agcaccaaaa agcaaggtcg aagaggaagt aaaccttc    58

<210> SEQ ID NO 16
<211> LENGTH: 46
<212> TYPE: DNA
<213> ORGANISM: Artificial Sequence
<220> FEATURE:
<223> OTHER INFORMATION: Primer

<400> SEQUENCE: 16
cgcgccgcgc gctagtctag agagtttgag taagccaaaa gatgag           46

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Leu Gln Asn Asp Ala Gln Ala Pro Lys Ser
1               5                   10

<210> SEQ ID NO 18
<211> LENGTH: 47
<212> TYPE: DNA
<213> ORGANISM: Artificial Sequence
<220> FEATURE:
<223> OTHER INFORMATION: Primer

<400> SEQUENCE: 18
gagacctcga gcagtcagca tgatagaaac atacagccaa ccttccc          47

<210> SEQ ID NO 19
<211> LENGTH: 39
<212> TYPE: DNA
<213> ORGANISM: Artificial Sequence
<220> FEATURE:
<223> OTHER INFORMATION: Primer
```

```
<400> SEQUENCE: 19
ccgcgcccca agcttatcag agtttgagta agccaaaag                             39

<210> SEQ ID NO 20
<211> LENGTH: 48
<212> TYPE: DNA
<213> ORGANISM: Artificial Sequence
<220> FEATURE:
<223> OTHER INFORMATION: Human ?Ct?TmCD40L+ Spacer Forward Primer
      (HCD40LSPF)

<400> SEQUENCE: 20
ctcgagaacg acgcacaagc accaaaatca catagaaggt tggacaag                   48

<210> SEQ ID NO 21
<211> LENGTH: 34
<212> TYPE: DNA
<213> ORGANISM: Artificial Sequence
<220> FEATURE:
<223> OTHER INFORMATION: Human CD40L reverse primer

<400> SEQUENCE: 21
cccaagcttt cagagtttga gtaagccaaa ggac                                  34
```